(12) United States Patent
Myers et al.

(10) Patent No.: US 6,682,559 B2
(45) Date of Patent: Jan. 27, 2004

(54) PROSTHETIC HEART VALVE

(75) Inventors: Keith Myers, Lake Forest, CA (US); Christine Nguyen, Garden Grove, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 164 days.

(21) Appl. No.: 09/772,526

(22) Filed: Jan. 29, 2001

(65) Prior Publication Data

US 2002/0052651 A1 May 2, 2002

Related U.S. Application Data

(60) Provisional application No. 60/178,333, filed on Jan. 27, 2000.

(51) Int. Cl.[7] .................................................. A61F 2/06
(52) U.S. Cl. ...................................... 623/2.13; 623/2.12
(58) Field of Search ............................... 623/1.24, 2.1, 623/2.12, 2.13, 2.15, 2.16, 2.33

(56) References Cited

U.S. PATENT DOCUMENTS

| | | |
|---|---|---|
| 3,608,097 A | 9/1971 | Bellhouse et al. |
| 3,671,979 A | 6/1972 | Moulopoulos |
| 4,056,854 A | 11/1977 | Boretos et al. |
| 4,106,129 A | 8/1978 | Carpentier et al. |
| 4,222,126 A | 9/1980 | Boretos et al. |
| 4,261,342 A | 4/1981 | Aranguren Duo |
| 4,274,437 A | 6/1981 | Watts |
| 4,297,749 A | 11/1981 | Davis et al. |
| 4,388,735 A * | 6/1983 | Ionescu et al. ............ 623/2.19 |
| 4,470,157 A | 9/1984 | Love |
| 4,501,030 A | 2/1985 | Lane |
| 4,624,822 A | 11/1986 | Arru et al. |
| 4,626,255 A | 12/1986 | Reichart et al. |
| 4,629,459 A | 12/1986 | Ionescu et al. |
| 4,787,901 A | 11/1988 | Baykut |

(List continued on next page.)

FOREIGN PATENT DOCUMENTS

| | | |
|---|---|---|
| EP | 0 051 451 A2 | 5/1982 |
| EP | 0 051 451 | 5/1982 |
| EP | 0 103 546 | 3/1984 |
| EP | 0 276 975 A1 | 8/1988 |
| EP | 0 515 324 A1 | 11/1992 |
| FR | 2 591 100 | 12/1985 |
| GB | 1 599 407 | 9/1981 |
| WO | WO 91/17720 | 11/1991 |
| WO | WO 91/19465 | 12/1991 |
| WO | WO 92/20303 | 11/1992 |
| WO | WO 00/42950 | 7/2000 |
| WO | WO 01/76510 A2 | 10/2001 |
| WO | WO 02/24118 A1 | 3/2002 |

OTHER PUBLICATIONS

Hubka, et al., *Replacement of mitral and tricuspid valves by mitral homograft*, The Journal of Thoracic and Cardiovascular Surgery, vol. 51 No. 2 Feb. 1966, pp. 195–204.

(List continued on next page.)

*Primary Examiner*—Corrine McDermott
*Assistant Examiner*—Thomas Barrett
(74) *Attorney, Agent, or Firm*—Jones Day

(57) ABSTRACT

A tubular prosthetic semilunar or atrioventricular heart valve is formed by cutting flat, flexible leaflets according to a pattern. The valve is constructed by aligning the side edges of adjacent leaflets so that the leaflet inner faces engage each other, and then suturing the leaflets together with successive stitches along a fold line adjacent the side edges. During operation, when the leaflets open and close, the leaflets fold along the fold line. Distal tabs extend beyond the distal end of each leaflet. The tab portions of adjacent leaflets are folded over each other and sewn together to form commissural attachment tabs. The commissural tabs provide commissural attachment points to accommodate sutures and the like in order to secure the tab to a vessel wall, if a semilunar valve, and papillary muscles and/or chordae tendineae, if an atrioventricular valve.

66 Claims, 15 Drawing Sheets

U.S. PATENT DOCUMENTS

| | | | |
|---|---|---|---|
| 4,790,844 | A | 12/1988 | Ovil |
| 4,960,424 | A | 10/1990 | Grooters |
| 5,032,128 | A | 7/1991 | Alonso |
| 5,037,434 | A | 8/1991 | Lane |
| 5,163,955 | A * | 11/1992 | Love et al. ............... 623/2.15 |
| 5,326,370 | A | 7/1994 | Love et al. |
| 5,332,402 | A | 7/1994 | Teitelbaum |
| 5,344,442 | A | 9/1994 | Deac |
| 5,370,685 | A | 12/1994 | Stevens |
| 5,411,552 | A | 5/1995 | Andersen et al. |
| 5,415,667 | A | 5/1995 | Frater |
| 5,480,424 | A | 1/1996 | Cox |
| 5,489,298 | A | 2/1996 | Love et al. |
| 5,500,015 | A | 3/1996 | Deac |
| 5,713,950 | A | 2/1998 | Cox |
| 5,713,953 | A | 2/1998 | Vallana et al. |
| 5,824,063 | A | 10/1998 | Cox |
| 5,824,065 | A | 10/1998 | Gross |
| 5,824,067 | A | 10/1998 | Gross |
| 5,928,281 | A | 7/1999 | Huynh et al. |
| 5,961,549 | A | 10/1999 | Nguyen et al. |
| 6,092,529 | A | 7/2000 | Cox |
| 6,129,758 | A | 10/2000 | Love |
| 6,254,636 | B1 * | 7/2001 | Peredo ............... 623/2.15 |
| 6,338,740 | B1 | 1/2002 | Carpentier |
| 6,350,282 | B1 | 2/2002 | Eberhardt |
| 6,454,799 | B1 | 9/2002 | Schreck |
| 6,461,382 | B1 | 10/2002 | Cao |

OTHER PUBLICATIONS

Holdefer, et al., *An experimental approach to mitral valve replacement with autologous pericardium*, The Journal of Thoracic and Cardiovascular Surgery, vol. 55 No. 6 Jun. 1968, pp. 873–881.

Akio Suzuki, M.D., et al., *Mitral valve replacement with transplant valves*, The Journal of Thoracic and Cardiovascular Surgery, vol. 60 No. 1 Jul. 1970, pp.13–25.

Mickleborogh, et al., *A Simplified Concept for a Bileaflet Atrioventricular Valve that Maintains Annular–Papillary Muscle Continuity*, The Journal of Thoracic and Cardiovascular Surgery, vol. 4 No. 1 Mar. 1989, pp. 58–65.

Athanasuleas, et al., *The autologous rectus sheath cardiac valve*, The Journal of Thoracic and Cardiovascular Surgery, vol.65 No. 1 Jan. 1973, pp. 118–123.

Endre Bodnar, M.D., et al., *Replacement Cardiac Valves*, Pergamon Press, (New York), 1991, pp. 307–332.

Charles S. Love, B.A., et al., *The Autogenous Tissue Heart Valve: Current Status*, Journal of Cardiac Surgery, vol. 6, No. 4, 1991.

W. Sterling Edwards, et al., *Partial and Complete Reconstruction of the Mitral Valve with Pericardium*, Prosthetic Heart Valves, 1969, pp. 820–831.

J.C. Van Der Spuy, *Completely anatomical autogenous whole mitral valve*, Thorax (1964), 19, pp. 526–529.

George Schimert, M.D., et al., *Fabrication of Mitral Leaflets and Aortic Cusps From Silastic Rubbercoated Teflon Felt*, Prosthetic Valves for Cardiac Surgery, pp.368–384.

* cited by examiner

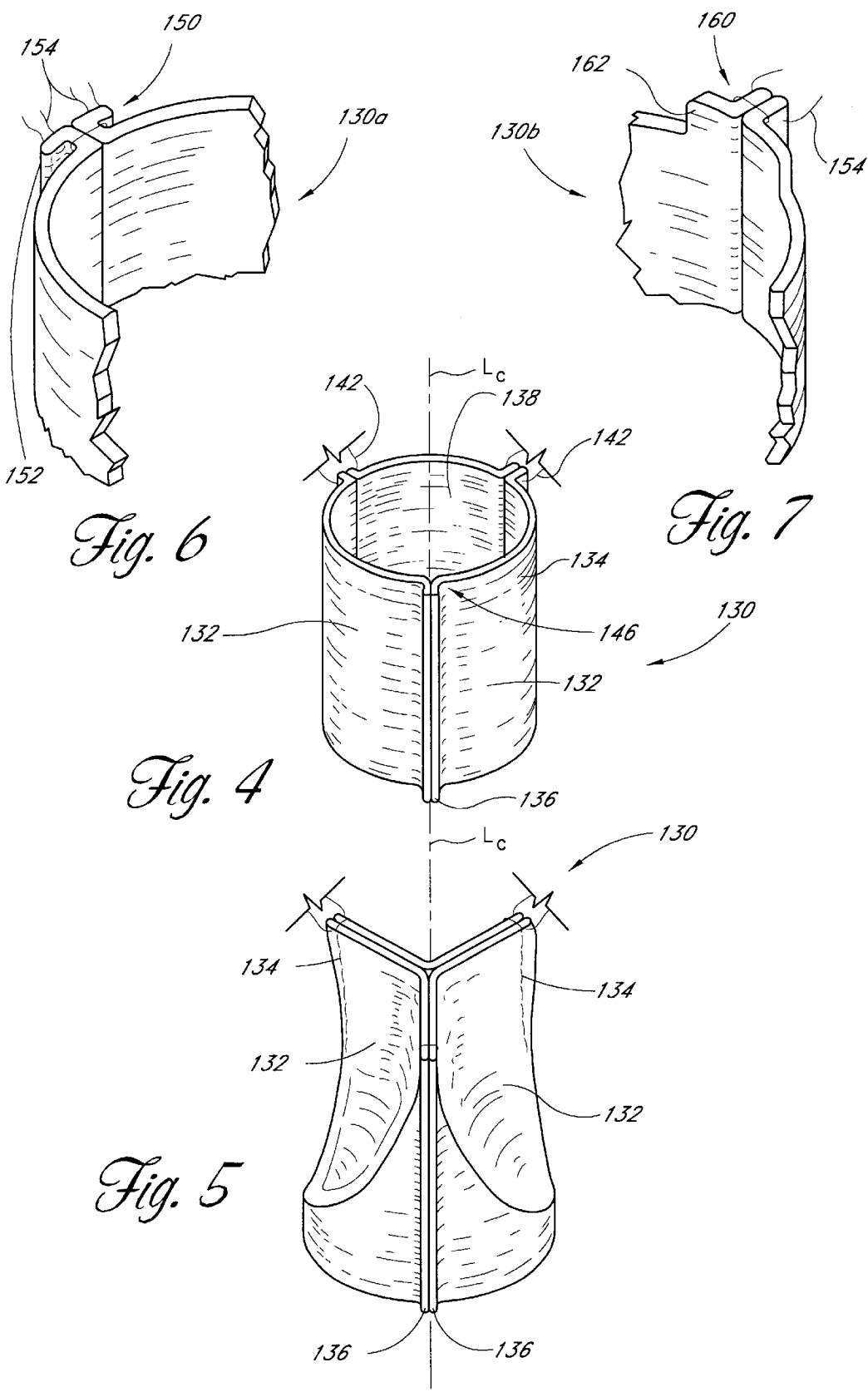

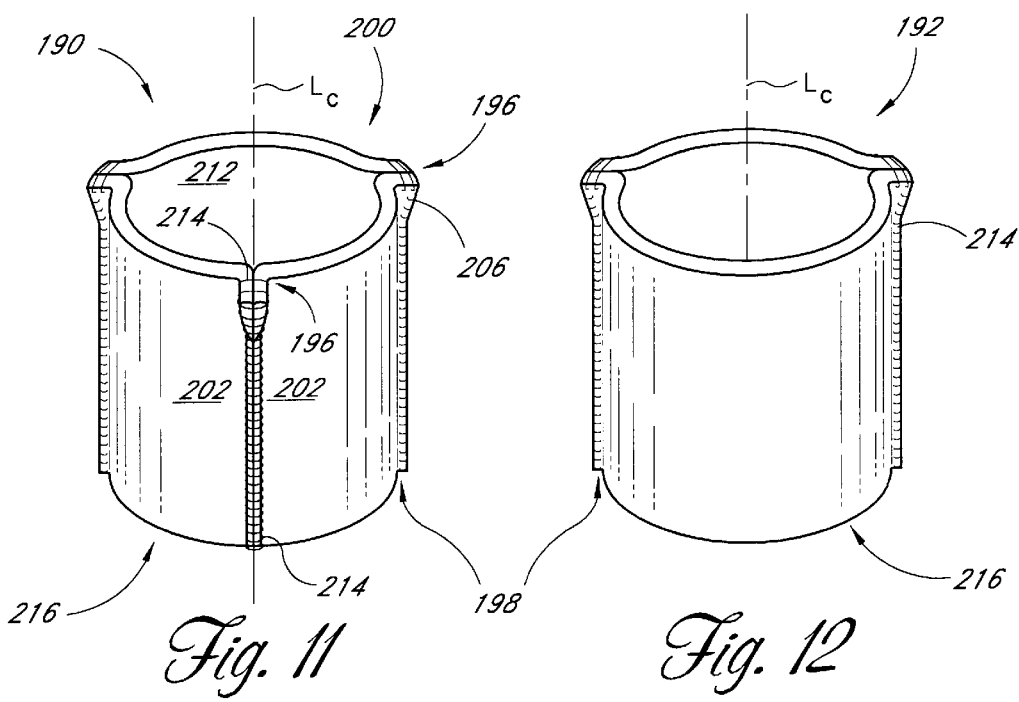
*Fig. 11*  *Fig. 12*
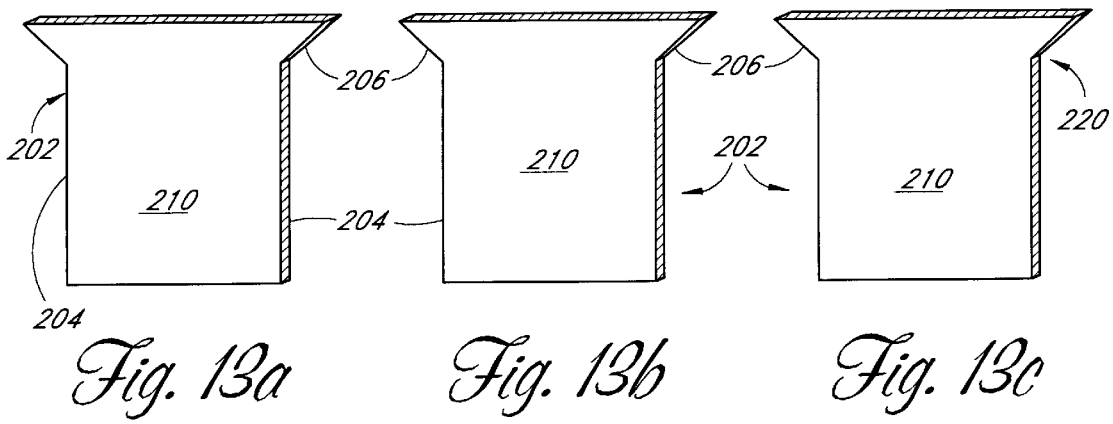
*Fig. 13a*  *Fig. 13b*  *Fig. 13c*
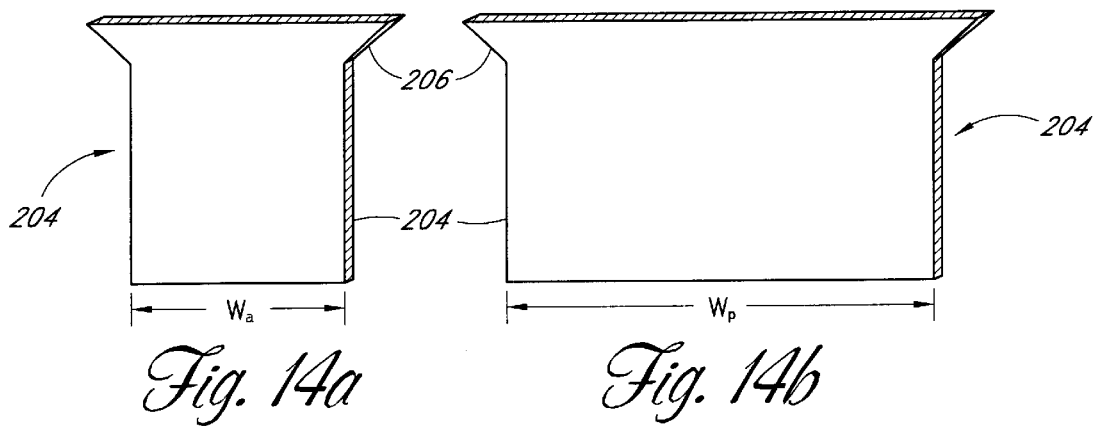
*Fig. 14a*  *Fig. 14b*

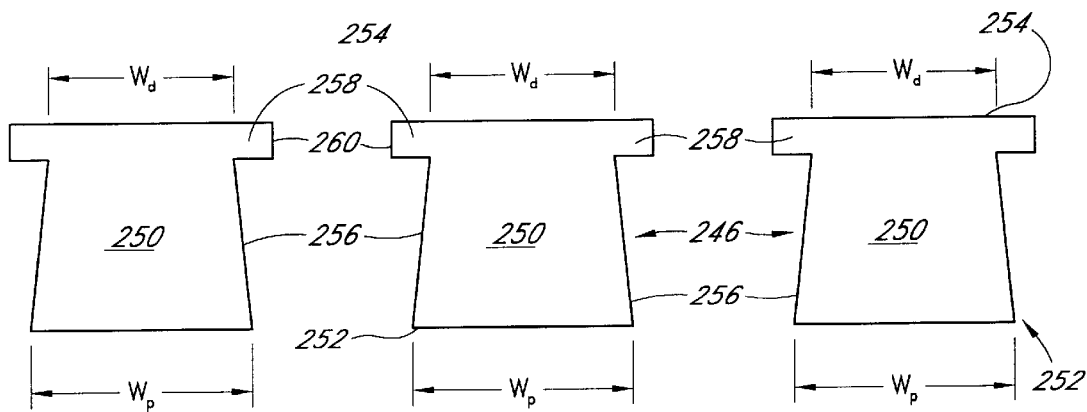
*Fig. 18a*   *Fig. 18b*   *Fig. 18c*
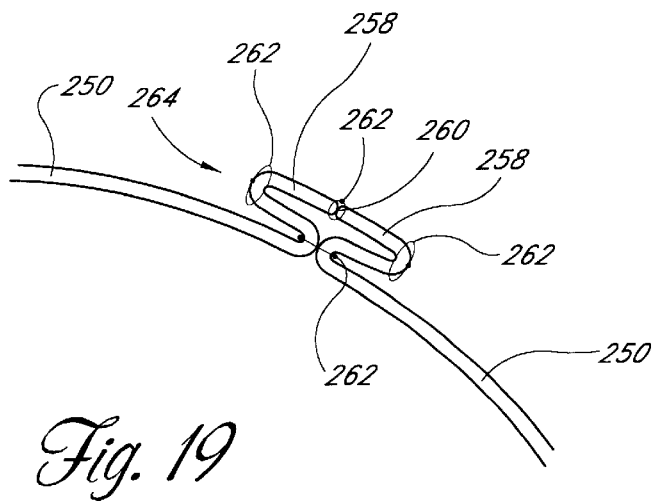
*Fig. 19*

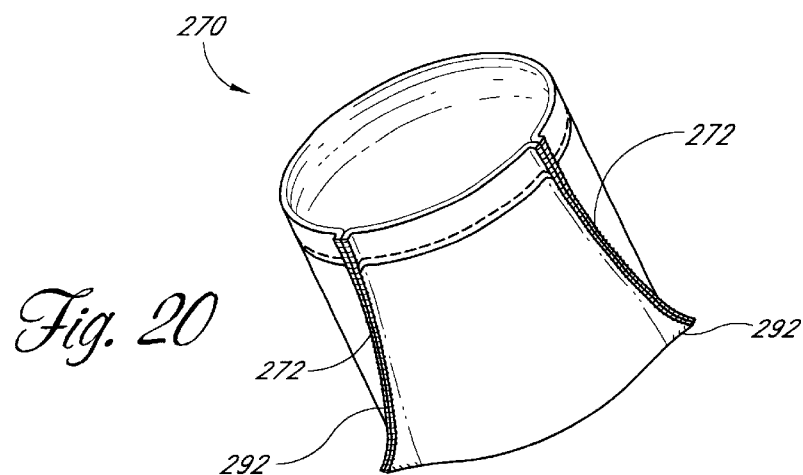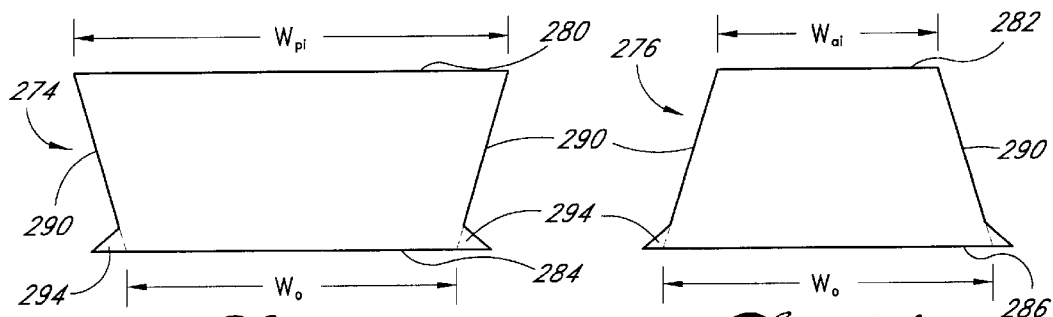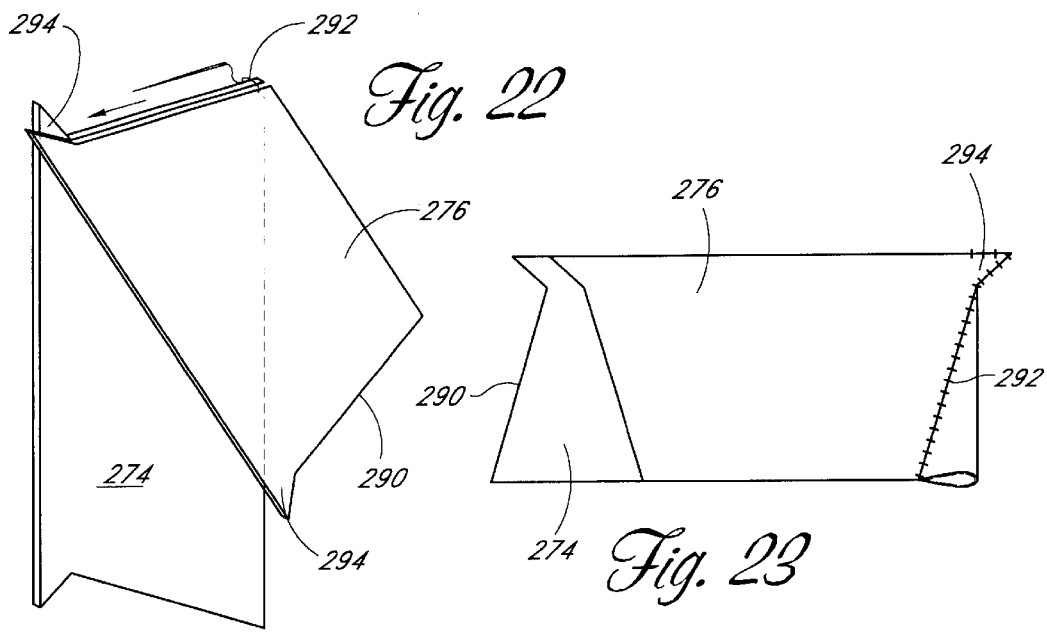

PROSTHETIC HEART VALVE

RELATED APPLICATIONS

This application claims priority to U.S. Provisional Application No. 60/178,333, filed Jan. 27, 2000, the entirety of which is hereby incorporated by reference.

BACKGROUND OF THE INVENTION

1. Field of the Invention

This invention relates to heart valves, and more particularly relates to replacement of diseased or injured heart valves.

2. Description of the Related Art

There are four valves in the heart that serve to direct blood flow through the two sides of the heart. On the left (systemic) side of the heart are: (1) the mitral valve, located between the left atrium and the left ventricle, and (2) the aortic valve, located between the left ventricle and the aorta. These two valves direct oxygenated blood from the lungs through the left side of the heart and into the aorta for distribution to the body. On the right (pulmonary) side of the heart are: (1) the tricuspid valve, located between the right atrium and the right ventricle, and (2) the pulmonary valve, located between the right ventricle and the pulmonary artery. These two valves direct de-oxygenated blood from the body through the right side of the heart and into the pulmonary artery for distribution to the lungs, where the blood becomes re-oxygenated in order to begin the circuit anew.

All four of these heart valves are passive structures in that they do not themselves expend any energy and do not perform any active contractile function. They consist of moveable "leaflets" that open and close in response to differential pressures on either side of the valve. The mitral and tricuspid valves are referred to as "atrioventricular valves" because they are situated between an atrium and ventricle on each side of the heart. The mitral valve has two leaflets and the tricuspid valve has three. The aortic and pulmonary valves are referred to as "semilunar valves" because of the unique appearance of their leaflets, which are shaped somewhat like a half-moon and are more aptly termed "cusps". The aortic and pulmonary valves each have three cusps.

Heart valves may exhibit abnormal anatomy and function as a result of congenital or acquired valve disease. Congenital valve abnormalities may be well-tolerated for many years only to develop a life-threatening problem in an elderly patient, or may be so severe that emergency surgery is required within the first few hours of life. Acquired valve disease may result from causes such as rheumatic fever, degenerative disorders of the valve tissue, bacterial or fungal infections, and trauma.

Since heart valves are passive structures that simply open and close in response to differential pressures on either side of the particular valve, the problems that can develop with valves can be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine whether the abnormal valve will have to be surgically replaced (or, in some cases, repaired).

Valve repair and valve replacement surgery is described and illustrated in numerous books and articles, and a number of options, including artificial mechanical valves and artificial tissue valves, are currently available. However, the currently-available options cannot duplicate the advantages of native (natural) heart valves. Some of the available mechanical valves tend to be very durable, but are problematic in that they are thrombogenic and exhibit relatively poor hemodynamic properties. Some of the available artificial tissue valves may have relatively low thrombogenicity, but lack durability. Additionally, even these artificial tissue valves often do not exhibit hemodynamic properties that approach the advantageous hemodynamic performance of a native valve. Some artificial tissue valves attempt to copy the form of native heart valves; such valves still fall short in durability and in hemodynamic performance.

James L. Cox, M.D. observed that during the natural embryological development, the human heart begins as a simple tubular structure, and changes its form during development based on its physiological function. Dr. Cox developed a tubular artificial heart valve, basing his research and development on the principle that "form follows function." This principle can be restated for heart valves as: "if an artificial valve can be created that truly functions like a native valve, its resultant form will be very similar to that of the native valve." The prosthetic heart valve that Dr. Cox developed based on this principle is discussed and disclosed in U.S. Pat. Nos. 5,480,424, 5,713,950 and 6,092,529. Each of these patents is hereby incorporated by reference in its entirety.

Dr. Cox's work has resulted in promising heart valve technology that can lead to the development of a prosthetic heart valve that can approach the overall performance of a native heart valve. Such a valve would be durable, nonthrombogenic, and would exhibit advantageous hemodynamics performance.

SUMMARY OF THE INVENTION

Accordingly, there is a need in the art for an improved prosthetic heart valve having advantageous hemodynamic performance, nonthrombogenicity, and durability.

In accordance with one aspect of the present invention, a stentless prosthetic heart valve includes a plurality of thin, flexible leaflets, each having an inner face, an outer face, an in-flow edge, an out-flow edge and side edges. The plurality of leaflets are sewn together along at a least a portion of their side edges so as to form a substantially tubular valve structure having an in-flow end and an out-flow end. The adjacent leaflets are arranged so that their side edges are substantially aligned and the inner faces of the leaflets engage each other adjacent the side edges. The valve structure is movable between a closed position in which the out-flow edges of adjacent leaflets engage each other, and an open position in which the out-flow edges of adjacent leaflets are separated from each other except along the side edges so that the sewn portions of the side edges of the leaflets bias the leaflets toward a partially closed position.

In accordance with another aspect of the present invention, a stentless semilunar heart valve includes three thin, flexible leaflets, each having an inner face, an outer face, an in-flow edge, an out-flow edge, side edges and tab portions extending outwardly beyond the side edges and positioned adjacent the out-flow edge such that the leaflets are attached to each other along their side edges so as to form a substantially tubular valve structure having an in-flow end and an out-flow end. The tab portions of adjacent leaflets engage each other to form commissural attachment tabs and at least a portion of each commissural attachment tab is adjacent to the outer face of the adjacent leaflets.

In accordance with yet another aspect of the present invention, a stentless heart valve has a first leaflet having a leaflet main body, the main body having an inner face, an outer face, a proximal end, a distal end, a first side edge, and a first tab portion adjacent the distal end and extending from the first side edge, the first tab portion connected to the first leaflet main body through a first neck portion; and a second leaflet having a leaflet main body having an inner face, an outer face, a proximal end, a distal end, a second side edge, and a second tab portion adjacent the distal end and extending from the second side edge, the second tab portion having a longitudinal slot and connected to the second leaflet main body through a second neck portion. The first side edge of the first leaflet and the second side edge of the second leaflet are substantially aligned with and attached to one another and the inner faces of the first leaflet and the second leaflet engage each other adjacent the aligned side edges. The second tab portion is folded so that the first and second neck portions extend through the longitudinal slot of the second tab portion. In addition, the neck portions of the leaflets are not stitched.

In accordance with a further aspect of the present invention, a method for making a stentless tubular prosthetic heart valve involves providing a section of substantially flat, flexible material, cutting a plurality of leaflets out of the flat material so that each of the leaflets has an inner face, an outer face, a proximal end, a distal end, side edges, and tab portions adjacent the distal end and extending from the side edges, aligning the side edges of adjacent leaflets together so that the inner faces of adjacent leaflets engage each other adjacent the side edges, and sewing aligned side edges together so as to form a substantially tubular valve structure having an in-flow end and an out-flow end. Additionally, the plurality of leaflets can be accomplished using a non-contact cutting apparatus, such as but not limited to a laser.

Another aspect of the present invention is a method for manufacturing a prosthetic heart valve involving providing a first valve leaflet and a second valve leaflet, the leaflets being formed separately from each other, placing a portion of an inward face of the first valve leaflet against a corresponding portion of an inward face of the second valve leaflet, and attaching the inward face portions to each other. The inward face portions of the leaflets are attached at the side edges of the leaflets.

Yet another aspect of the present invention involves a method of manufacturing a heart valve involves providing first and second valve leaflets each having an integral tab portion at an end thereof, and folding the tab portions relative to each other to provide a commissural tab, the commissural tab being attached to the leaflets along a commissural tab line such that free ends of the tabs extend outwardly from the line.

In accordance with another aspect of the present invention, a prosthetic valve includes a plurality of valve leaflets comprised of a flexible material, each leaflet having an inner surface and an outer surface, each leaflet attached to another leaflet along an attachment line, a portion of an inner surface face of one leaflet being in facing relationship with a portion of an inner surface of another leaflet at the attachment line, and a commissural tab at an end of each attachment line. The tab having free ends configured for attachment to a blood vessel.

In accordance with another aspect of the present invention, the leaflets of a prosthetic valve are comprised of equine pericardium. The pericardium is fixed, such as in a glutaraldehyde solution.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 4 shows another embodiment of a tubular prosthetic heart valve having features in accordance with the present invention, shown in an open position.

FIG. 5 shows the valve of FIG. 4 in a closed position.

FIG. 6 is a close-up cutaway view of a portion of another embodiment of a heart valve similar to the valve of FIG. 4.

FIG. 7 is another close-up cutaway view of a portion of still another embodiment of a heart valve similar to the valve of FIG. 4.

FIG. 11 shows a perspective view of another embodiment of a tubular prosthetic aortic heart valve having attachment tabs adjacent a downstream end thereof.

FIG. 12 shows a perspective view of an embodiment of a tubular prosthetic mitral heart valve having attachment tabs adjacent a downstream end thereof.

FIGS. 13A–C show flat patterns of individual leaflets of the valve of FIG. 11.

FIGS. 14A–B show flat patterns of individual leaflets of the valve of FIG. 12.

FIGS. 18A–C show flat patterns for the leaflets of the heart valve of FIG. 19.

FIG. 19 shows a sectional view of a commissural attachment tab of the valve of FIG. 17, taken along line 19—19.

FIG. 20 shows a perspective view of a prosthetic mitral heart valve having features in accordance with the present invention and having slanted seam lines.

FIG. 21A shows a flat leaflet pattern for a posterior leaflet of the valve of FIG. 20.

FIG. 21B shows a flat pattern for an anterior leaflet of the valve of FIG. 20.

FIG. 22 shows an initial step of suturing the posterior and anterior leaflets of FIGS. 21A and 21B together.

FIG. 23 shows yet a further step of suturing the posterior and anterior leaflets of FIGS. 21A and 21B together.

DETAILED DESCRIPTION OF THE PREFERRED EMBODIMENT

Figure 1:
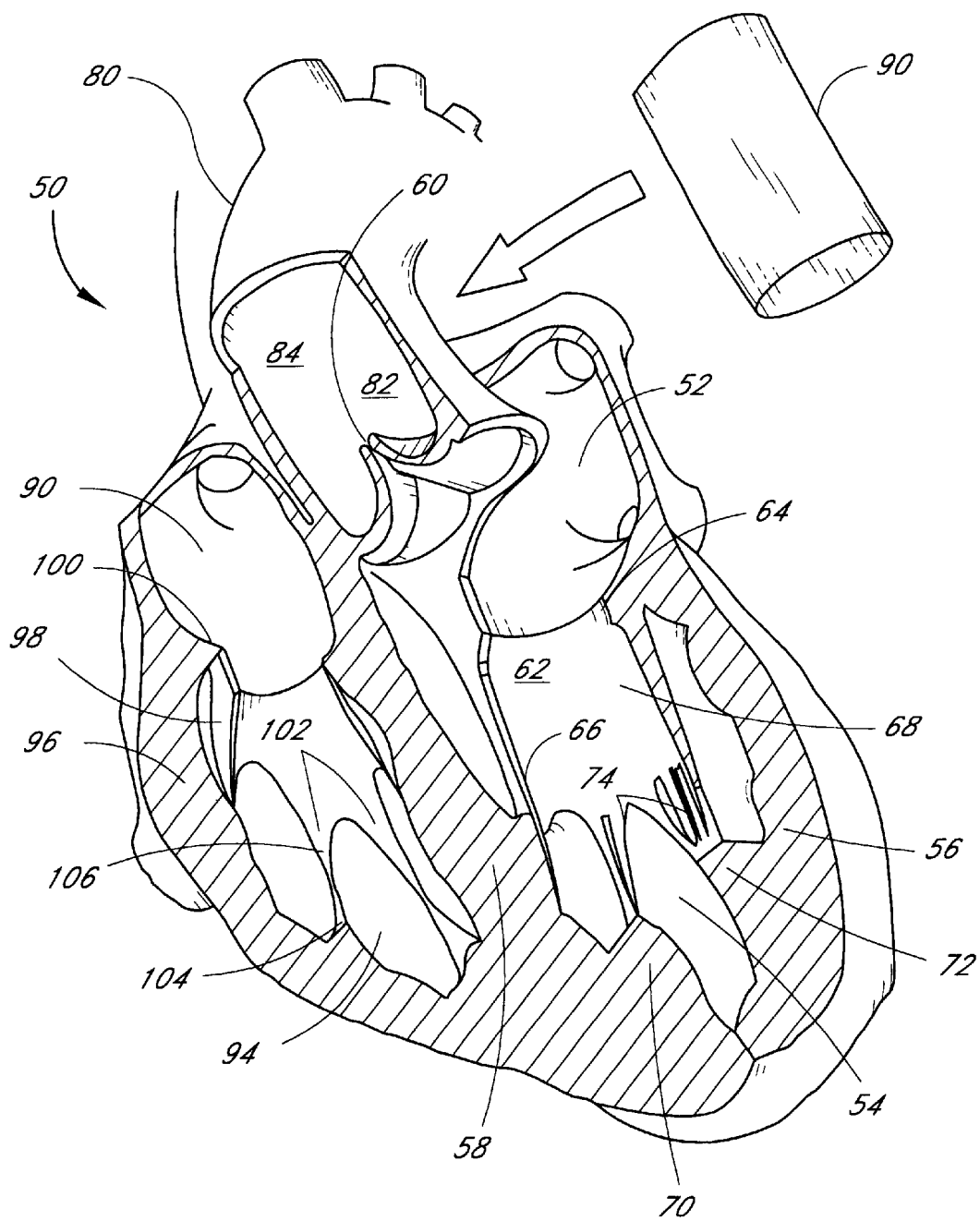
FIG. 1 is a partial cutaway view of a human heart showing the placement of a tubular heart valve in the location of the native aortic valve.

FIG. 1 shows a cross-sectional cutaway depiction of a normal human heart 50. The left side of heart 50 contains a left atrium 52, a left ventricular chamber 54 positioned between a left ventricular wall 56 and a septum 58, an aortic valve 60, and a mitral valve assembly 62. The components of the mitral valve assembly 62 include a mitral valve annulus 64; an anterior leaflet 66 (sometimes called the aortic leaflet, since it is adjacent to the aortic region); a posterior leaflet 68; two papillary muscles 70 and 72, which are attached at their bases to the interior surface of the left ventricular wall 56; and multiple chordae tendineae 74, which couple the mitral valve leaflets 66 and 68 to the papillary muscles 70 and 72. There is no one-to-one chordal connection between the leaflets and the papillary muscles; instead, numerous chordae are present, and chordae from each papillary muscle 70 and 72 attached to both of the valve leaflets 66 and 68.

The aorta 80 extends generally upwardly from the left ventricular chamber 54, and the aortic valve 60 is disposed within the aorta 80 adjacent the left ventricle 54. The aortic valve 60 comprises three cusps 82, or leaflets. Portions of each leaflet 82 are attached to the aortic wall 84 at commissural points. Shown next to the aorta 80 is a segment of tubular tissue 90 which can be used to replace the aortic valve 60 in a manner as described below.

The right side of the heart 50 contains a right atrium 92, a right ventricular chamber 94 bounded by a right ventricular wall 96 and the septum 58, and a tricuspid valve assembly 98. The tricuspid valve assembly 98 comprises a valve annulus 100, three leaflets 102, papillary muscles 104 attached to the interior surface of the right ventricular wall 96, and multiple chordae tendineae 106, which couple the tricuspid valve leaflets 102 to the papillary muscles 104.

The right ventricular chamber 94 opens into a pulmonary artery (not shown) which leads from the chamber to the lungs. A pulmonary valve (not shown) is disposed within the pulmonary artery and regulates blood flow from the right ventricular chamber 94 into the pulmonary artery.

The mitral and tricuspid valve leaflets, as well as the aortic and pulmonary valve cusps, are all passive structures; they do not themselves expend any energy and do not perform any active contractile function. They are designed to simply open and close in response to differential pressures on either side of the valve.

When the left ventricular wall 56 relaxes so that the ventricular chamber 54 enlarges and draws in blood, the mitral valve 62 opens (i.e., the leaflets 66 and 68 separate) and the aortic valve cusps 82 approximate one another to close the aortic valve 60. Oxygenated blood flows through the mitral valve 62 to fill the expanding ventricular cavity 54. The approximated aortic valve cusps 82 prevent blood that has entered the aorta 80 from leaking (regurgitating) back into the left ventricle. Once the left ventricular cavity 54 has filled, the left ventricle contracts, causing a rapid rise in the left ventricular cavitary pressure. This causes the mitral valve 62 to close (i.e., the leaflets 66 and 68 re-approximate) while the cusps 82 of the aortic valve 60 open, allowing the oxygenated blood to be ejected from the left ventricle 54 into the aorta 80. The chordae tendineae 74 of the mitral valve prevent the mitral leaflets 66 and 68 from prolapsing back into the left atrium 52 when the left ventricular chamber 54 contracts. Neither of the semilunar valves (aortic and pulmonary) has associated chordae tendineae or papillary muscles.

The three leaflets 102, chordae tendineae 106, and papillary muscles 104 of the tricuspid valve 98 function in a manner similar to the mitral valve 62. The pulmonary valve cusps respond passively in response to relaxation and contraction of the right ventricle in moving de-oxygenated blood into the pulmonary artery and thence to the lungs for re-oxygenation.

In summary, with relaxation and expansion of the ventricles (diastole), the mitral and tricuspid valves open, while the aortic and pulmonary valves close. When the ventricles contract (systole), the mitral and tricuspid valves close and the aortic and pulmonary valves open. In this manner, blood is propelled through both sides of the heart.

As discussed above, it is sometimes necessary to replace a native heart valve with a prosthetic valve. The native valve can be removed by cutting about the valve annulus and, in atrioventricular valves, cutting the corresponding papillary muscles and/or chordae tendineae, or, in semilunar valves, cutting out the valve's commissural attachment points. Once the native valve is removed, a replacement valve's in-flow annulus is attached, through sutures or other attachment methods, to the valve annulus vacated by the native valve. Downstream portions of the replacement valve are preferably attached to commissural attachment points or papillary muscles and/or chordae tendineae, as described below.

A number of embodiments of tubular prosthetic heart valves are described below. These embodiments illustrate and describe various aspects of the present invention. Embodiments of aortic valves and mitral valves are discussed and presented below; however, it is to be understood that the aspects discussed in relation to these valves can be applied to any type of heart valve. Accordingly, even though the leaflets of semilunar valves such as the aortic and pulmonary valves are more aptly termed "cusps" than "leaflets," the discussion refers to both the cusps of semilunar valves and the leaflets of atrioventricular valves as "leaflets."

Figure 2:
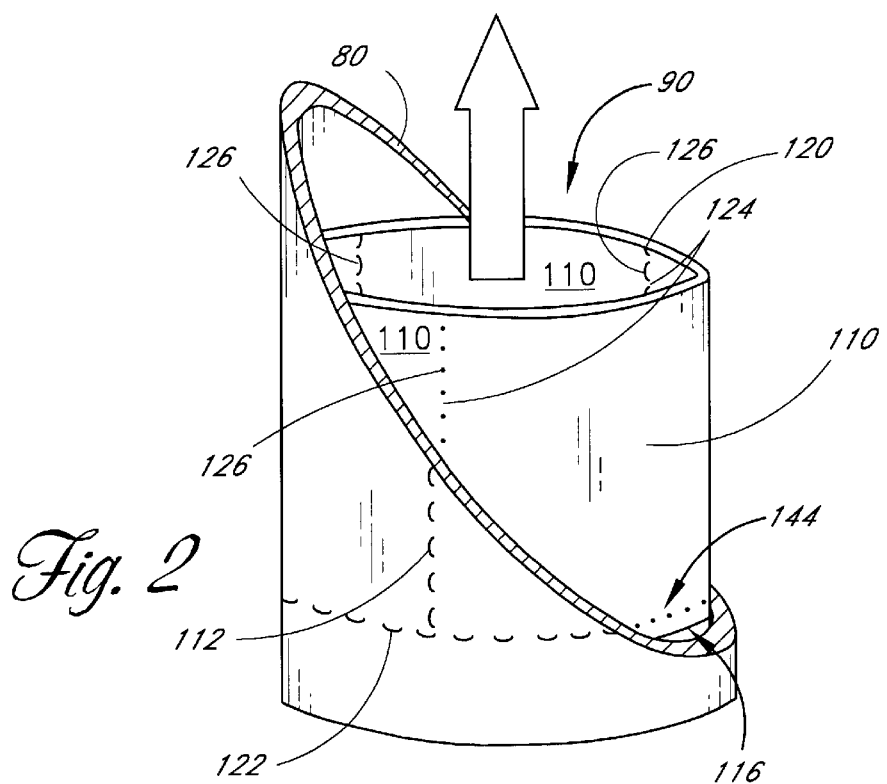
FIG. 2 shows a prosthetic tubular heart valve in accordance with the present invention mounted within a patient's aorta, portions of which are cut away, and the valve is shown in an open position.
Figure 3:
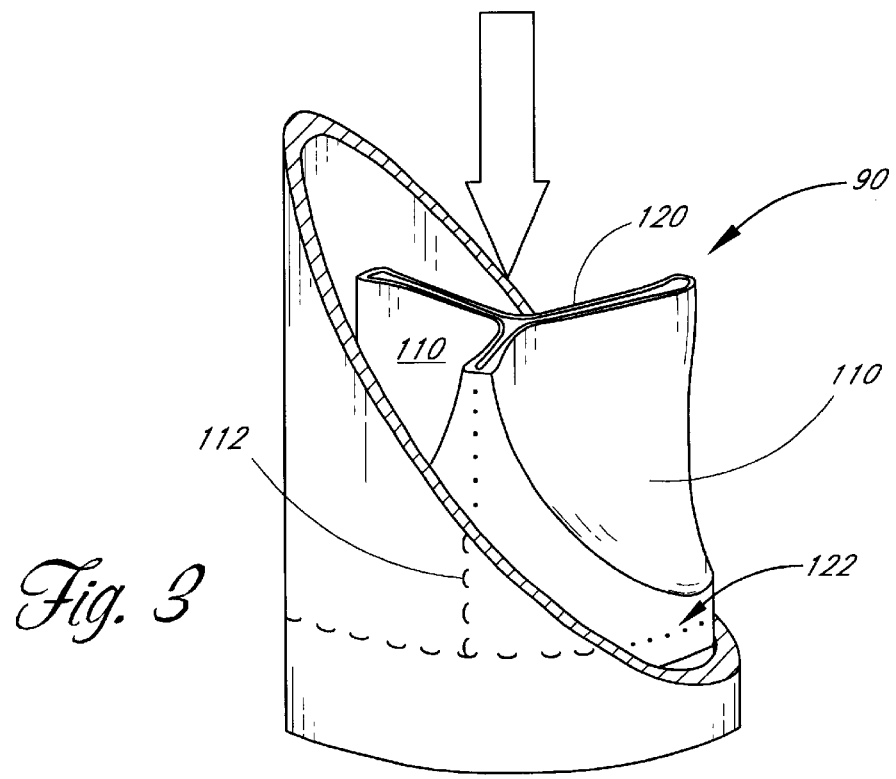
FIG. 3 shows the valve of FIG. 2 in a closed position.

FIGS. 2 and 3 show the tubular prosthetic heart valve 90 shown in FIG. 1 installed within a patient's aorta 80, with the aortic wall 84 partially cut away in order to show the valve. As shown, the valve 90 preferably comprises three leaflets 110. Each leaflet 110 is constructed of a flat, flexible biological tissue or artificial material. The leaflets 110 are attached to one another along seam lines 112 so as to form a tubular valve 90. The tubular valve has an in-flow annulus 114 at a proximal end 116 of the valve and an out-flow annulus 118 at a distal end 120 of the valve. An annular seam 122 about the in-flow annulus 114 of the valve secures the valve to the aortic wall 84 at the in-flow annulus 114 in a manner so that blood flows through the valve 90 and not between the aortic wall 84 and the valve 90. In this manner, during systole, shown in FIG. 2, the leaflets 110 are forced apart so that blood flows freely through the tubular valve and into the aorta 80 in the direction shown by the arrow.

The valve 90 is attached to the aortic wall 84 at three commissural attachment sites 124. Preferably no stent or frame is used to hold the valve in place. The commissural attachment sites 124 preferably lie along the seam lines 112, and the valve 90 is preferably attached to the aortic wall 84 with attachment sutures 126.

With next reference to FIG. 3, during diastole, differential pressures urge blood toward the ventricle as indicated by the direction arrow. The leaflets 110 are thus drawn toward each other and approximate each other, sealing the valve and preventing regurgitation of blood through the valve from the aorta 80 into the ventricle. The commissural attachment sites 124, which attach the downstream ends of the valve 90 to the aortic wall 84, prevent the leaflets 110 from prolapsing. This enables the leaflets 110 to engage each other as shown so that a sealing closure of the valve is achieved.

In a preferred embodiment, the flexible material comprises equine pericardium that has been cross-linked and fixed in a low-concentration, buffered glutaraldehyde solution. Applicants have determined that equine pericardium is about half as thick and just as strong as bovine pericardium, which is used in some prosthetic heart valves. The decreased thickness of the equine pericardium results in leaflets that are more pliable and easier to open and close than leaflets in previously-available artificial valves. The material is also easier to work with and thus allows greater precision when constructing the valve.

Although equine pericardium is used in the illustrated embodiments, it is to be understood that a number of materials, both biological and man-made, can be employed. For example, bovine, porcine and kangaroo pericardial tissue may be appropriately used. Also, man-made materials, such as polyesters, Teflon®, woven or knitted cloths, etc., can also be advantageously used. Materials can be selected using a general guideline that the more pliable, thin and strong the material is, the better. Additionally, it is advantageous for the material to be as nonthrombogenic as possible.

During use, the valve 90 will repeatedly cycle between the open and closed positions demonstrated in FIGS. 2 and 3. As can be seen, during closure, the leaflets 110 fold generally about the commissural attachment sites 124. Since the leaflets 110 will repeatedly fold about the commissural attachment sutures 126 during use of the valve, the sutures may interfere with the normal and natural motion of the valve leaflets 110 during closure. Also, due to the motion of the leaflets 110 about the sutures 126, the commissural attachment site 124 could become a site for wear or abrasion of the leaflets. Further, since the commissural attachment points 124 bear much of the closure force during diastole, the sutures may become points of significant stress concentration, especially the distal-most sutures. The above conditions can significantly reduce the durability of the commissural attachment points 124. These concerns are addressed and resolved in some of the embodiments that follow.

With next reference to FIGS. 4 and 5, another embodiment of a tubular aortic heart valve 130 is shown in an open (FIG. 4) and closed (FIG. 5) orientation. The heart valve 130 comprises three flexible leaflets 132 that are sewn to each other along a seam line 134 adjacent their side edges 136. Each leaflet 132 has an inner surface 138 and an outer surface 140. The side edges 136 of adjacent leaflets are sewn together so that the inner surfaces 138 of the sewn-together leaflets 132 face each other, and the side edges 136 extend generally radially outwardly relative to a longitudinal center line $L_c$ of the valve 130. This arrangement provides a number of advantages. For example, the leaflets 132 are naturally biased partially toward the closed position. This enables easier and more natural closure of the valve. Also, closure is more complete, especially in the area near the seam line 134. Further, the leaflets 132 are sewn together in a manner so that the leaflet edges 136 can be sewn tightly together in a manner to minimize leaking between leaflets and to maximize seam strength and durability. Still further, commissural attachment sutures 142, which attach the valve 130 to the aortic wall, can attach to folded-back portion 146 of the valve between the seam line 134 and the side edges 136 of the leaflets 132. In this arrangement, the commissural attachment sutures 142 are, in effect, isolated from the folding portions of the leaflets 132 so that the folding leaflets do not rotate about or move relative to the attachment sutures 142. Thus, the attachment sutures 142 do not interfere with leaflet movement or cause wear and abrasion of the leaflets 132.

With next reference to FIGS. 6 and 7, additional embodiments of heart valves 130A, 130B employ commissural tabs 150. The commissural tabs 150 are dedicated to providing commissural attachment sites that are isolated from the folding leaflets 132 in order to improve durability and to provide an easy, visible target for the surgeon to place commissural sutures on when implanting the valve.

With specific reference to FIG. 6, a tab portion 154 of adjacent leaflets 132 between the seam line 134 and the side edge 136 are extended somewhat in a distal portion of the valve 130A. The extended portions 152 are folded back so as to be generally parallel to the outer face 140 of the corresponding leaflet 132. This results in a pair of tab portions 152 that extend behind the valve and substantially tangential to the open valve. Each of the tabs 152 can be connected to the aortic wall by a suture 154. Thus, at least two sutures are used to attach the commissural tabs 150 to the aortic wall. These sutures are substantially isolated from the folding portions of the leaflets. Also, the force exerted on the commissural site is distributed over multiple sutures, thus reducing the significance and impact of individual stress concentrations.

With next reference to FIG. 7, an additional embodiment of a dedicated commissural tab 160 comprises a raised portion 162 of the leaflets 132 positioned adjacent the seam line 134 and extending distally from the distal end of the adjacent leaflets. One or more commissural attachment sutures 154 can be used to attach the raised commissural tab 160 to the aortic wall. The raised tab 160 makes an easy target for a surgeon to place sutures on, and also aids in distributing forces during valve operation. For example, during diastole, when differential pressures urge the leaflets to the closed position, the raised tab 160 allows the commissural sutures 154 to be positioned at a site further removed from the distal end of each leaflet, thus further isolating the commissural tabs 160 from the leaflets 132 so that the commissural sutures have even less of an effect on closure activity of the valve. Additionally, significant portions of the forces exerted on the valve during closure are focussed along the distal end of the valve. By positioning multiple commissural sutures distal of the valve's distal end, these closure forces can be distributed across multiple sutures. Thus, stresses on the individual sutures are relatively reduced.

Figure 9:
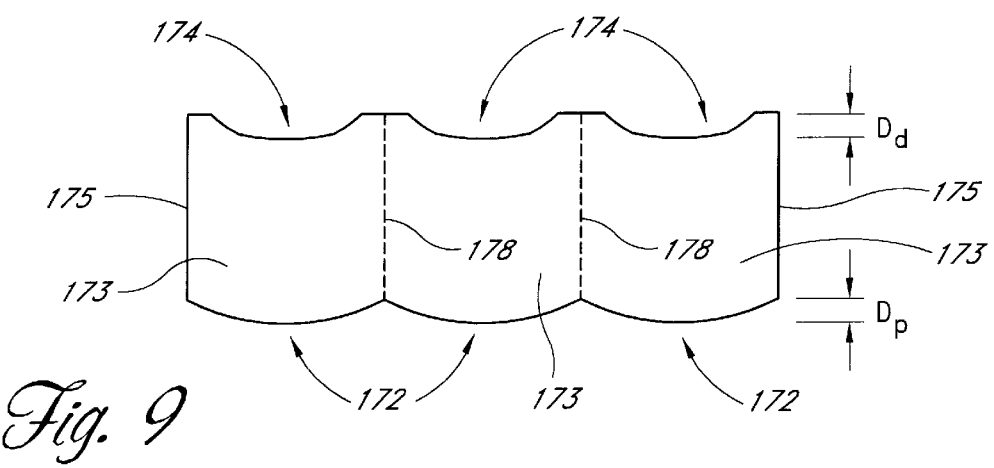
FIG. 9 shows a pattern from which leaflets of the valve of FIG. 8 may be created.
Figure 8A:
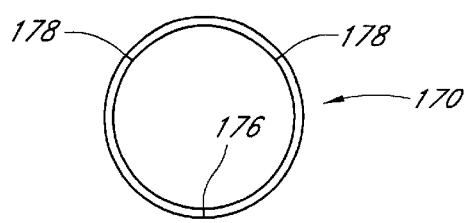
FIG. 8A is a top view of the scalloped tubular prosthetic valve of FIG. 8.
Figure 8:
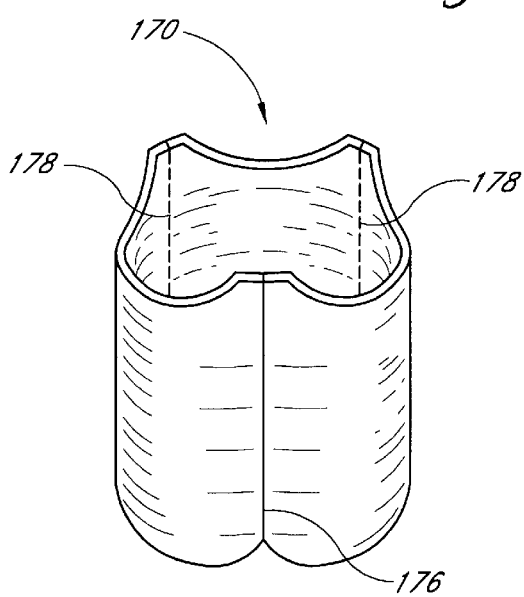
FIG. 8 is a perspective view of a scalloped tubular prosthetic heart valve having features in accordance with the present invention.

With next reference to FIGS. 8 and 9, a still further embodiment of a tubular aortic heart valve 170 having features in accordance with the present invention is illustrated. The valve 170 has scalloped in-flow and out-flow leaflet edges 172, 174. As shown in FIG. 9, the three leaflets 173 are preferably cut from a single piece of flat, flexible material. The side edges 175 are preferably sewn together at a main seam line 176, forming a substantially tubular valve, as shown in FIG. 8A. Longitudinal seam lines 178 are stitched to define the leaflets and to aid valve closure.

Applicants have discovered through testing that scalloping aids in the closure and hemodynamic performance of the valve. As discussed above, advantageous hemodynamic performance is desired in heart valves. A heart valve having advantageous hemodynamic performance will allow blood to flow smoothly and efficiently therethrough. On the other hand, problems with hemodynamics result in excessive turbulence and possible pooling of blood. This can lead to various problems, notably calcification, in which calcium deposits build up on the heart valve, eventually impairing the valve's ability to function.

During development and testing of a straight-edged tubular embodiment of a heart valve, it was observed that some redundant material was present at the out-flow end of the valve during closure of the valve. This redundant material caused excessive folding and creasing at the out-flow edge of the valve. The in-flow edge of the straight-edged tubular embodiment was also inspected and observed during physiologic closure testing, revealing creasing at the leaflet edges near the in-flow annulus. Additionally, scalloping the in-flow edge facilitates a better fit of the prosthetic valve in the annulus vacated by the native valve.

Through continued development and testing, Applicants have determined that scalloping both the in-flow and out-flow edges 172, 174 of each leaflet helps to maximize the valve's hemodynamic performance and to minimize creasing and folding, which may have long-term, negative effects on valve durability, as well as closure capability.

As can be seen in FIGS. 8 and 9, the scalloping adjacent the in-flow annulus 176 is such that the center portion of the leaflet extends proximally beyond the proximal end of the leaflet adjacent the seam line 178. The distance DP between the proximal end 172 of each leaflet at a point adjacent the seam line 178 and at the center of the leaflet has been determined through testing to preferably be between about 15%–25% of the overall diameter of the valve, and most preferably about 20% of the diameter of the valve. The scalloping shape preferably follows a smooth curve.

At the distal end 174 of the valve, the center portion of each leaflet is preferably positioned a distance $D_d$ proximal of the distal end of the leaflets adjacent the seam line 178. This distance $D_d$ has been determined through testing to be preferably between about 8%–20% of the overall diameter of the valve, and is more preferably between about 15%–17% of the diameter of the valve. As with the inflow annulus, the scalloping shape preferably follows a smooth curve.

Figure 10:
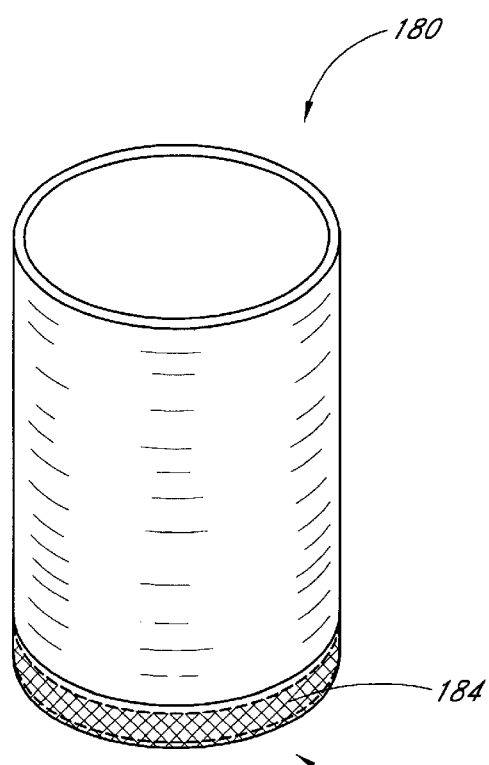
FIG. 10 shows another embodiment of a tubular prosthetic heart valve in accordance with the present invention and having an annular sewing cuff.

The in-flow annulus sustains significant forces during the repeated opening and closing of the valve and during the pulsed flow of blood through the valve and aorta. Accordingly, another embodiment of the present invention provides tubular valve 180 having a reinforcement at the in-flow annulus 182. With next reference to FIG. 10, an annular sewing cuff 184 can be provided at the in-flow annulus 182 to provide reinforcement at the in-flow annulus 182. In a preferred embodiment, the sewing cuff 184 comprises a woven or knitted cloth material, preferably a polyester material, that is sutured or otherwise attached to the valve's in-flow annulus 182. The woven cloth enables fibrous tissue from the aorta to grow into and around the reinforcement material, further securing the cuff and valve to the aortic wall, and better establishing a seal between the in-flow annulus 182 and the aortic wall. Additionally, as tissue grows into and around the woven material, natural cells are deposited between the blood flow and the man-made material, effectively isolating the man-made cloth material from the blood flow. The thrombogenicity of the material is thus reduced or even eliminated because blood flowing through the valve is separated from the material by the tissue. A thin layer of endothelial cells, which typically line the entire inner surface of the vascular system, can be expected to line portions of the annulus 182.

Although the sewing cuff 184 is shown in use on a simple tubular valve 180, it is to be understood that such a woven or knitted sewing cuff can be used in any of the embodiments discussed above or below, including scalloped embodiments. Additionally, other suitable materials, such as pericardium, can be used for providing the extra reinforcement provided by the sewing cuff.

With next reference to FIGS. 11 and 12, additional embodiments of an aortic 190 (FIG. 11) and a mitral 192 (FIG. 12) tubular prosthetic heart valve are shown. In these embodiments, commissural attachment tabs 196 are provided along the seam lines 198 adjacent the distal/out-flow ends 200 of the valves. The illustrated attachment tabs 196 have a generally triangular "dog ear" shape. The manner in which these valves are constructed is discussed below and illustrated in FIGS. 13–15.

The aortic valve 190 of FIG. 11 is constructed by connecting three leaflets 202. With reference next to FIGS. 13A–C, the leaflets 202 are preferably cut out of a thin, flat, flexible material such as the equine pericardium discussed above. Edge portions 204 of each leaflet extend outwardly adjacent the distal end 200 of the leaflet, forming substantially triangular tab portions 206 extending from a main body 210 of the leaflet 202.

Figure 15:
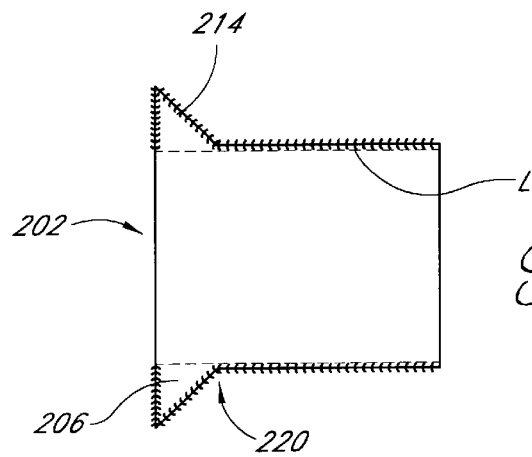
FIG. 15 shows a suturing arrangement of the leaflets of FIGS. 13A–C, showing the location of seams holding adjacent leaflets together.

FIG. 15 shows a stitching pattern for constructing the valve 190. Adjacent leaflets 202 are stitched together along their side edge 204 with their inner surfaces 212 facing each other, as with the embodiment discussed in connection with FIGS. 4 and 5. Thus, the inner surfaces 212 of adjacent leaflets 202 engage each other and the side edges 204 of each leaflet 202 extend radially outwardly from a center line $L_c$ of the valve 190.

A preferred method of suturing adjacent leaflets together comprises first making a conventional triple loop using a sewing needle and then forming a series of stitches 214, preferably buttonhole-type stitches followed by locking knots, beginning at the inflow end 216 of the valve 190 and extending toward the out-flow end 200 of the valve along a substantially straight seam line L adjacent the leaflet edge (see FIG. 15). The stitches 214 along the edges 204 are spaced preferably approximately 1 millimeter from the edges and are spaced 1 to 1-½ millimeters apart. Preferably, a double loop or another type of locking stitch is provided to lock each stitch. Using a buttonhole stitch followed by a locking knot allows the integrity of the entire seam to be preserved even if the seam is cut or broken.

When the stitching reaches the proximal end 220 of the distal tab 206, the stitching ceases to follow the seam line L, and successive stitches 214 are instead tied following the outer edge along the tab 206. When the stitching has been completed to the distal end 200 of the leaflet, successive stitches are tied along the distal edges 200 in a direction toward the line L until a stitch is tied at a position substantially adjacent the intersection of the line L and the distal end of the leaflet. In this manner, adjacent leaflets 202 are securely attached to one another and a commissural attachment tab 196 is formed generally separated from the main body 210 of the leaflets 202.

The commissural attachment tabs 196 are adapted to receive commissural attachment sutures (not shown) to attach the valve to commissural attachment points. The "dog-ear" commissural attachment tabs shown in FIGS. 11–15 comprise two overlapping layers of adjacent leaflets. This provides reinforcement at the distal commissural attachment points, thus improving long-term durability for the prosthetic valves.

In the illustrated embodiments, the knotted stitching does not extend along line L in the distal-most portion of the leaflets 202. This reduces the possibility that stitching along the seam line L will interfere with leaflet closure; thus, stress concentrations and possible friction and wear associated with leaflets folding about locked stitches during repeated opening and closing of the valves is minimized.

With next reference to FIGS. 12 and 14, for a mitral valve 192, the anterior leaflet 224 (FIG. 14A) is generally smaller than the posterior leaflet 226 (FIG. 14B). In the illustrated embodiment, the anterior leaflet 224 has a width $W_a$ generally about one half of the width of the posterior leaflet $W_p$. The adjacent leaflets are sewn together in the manner discussed above, resulting in a 2-leaflet mitral valve 192 having dog-eared commissural attachment tabs 196, as shown in FIG. 12.

Figure 16:
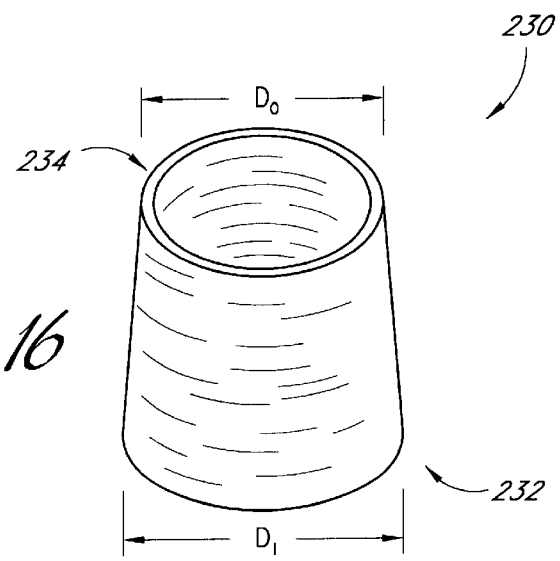
FIG. 16 shows a perspective view of a tapered prosthetic aortic heart valve having features in accordance with the present invention.

With next reference to FIG. 16, another embodiment of a prosthetic heart valve 230 having features in accordance with the present invention comprises a tubular valve wherein the valve 230 is tapered from the in-flow annulus 232 to the out-flow annulus 234. As shown, the diameter $D_o$ of the out-flow annulus 234 is less than the diameter $D_i$ of the in-flow annulus 232. This embodiment was developed as a solution to a problem identified by Applicants during development and testing of valves. Additionally, in aortic valves, the commissural attachment points are located in a portion of the aorta that has a slightly smaller diameter than the diameter at the valve annulus.

Applicants discovered during testing of a substantially cylindrical tubular valve that, during closure of the valve, the distal ends of the valve leaflets tended to fold somewhat, thus disrupting the smooth engagement of adjacent leaflets and adversely affecting the sealing of the valve. Applicants noted that the generally circular out-flow annulus 234 has a circumference of $\pi D$, with D denoting the valve's diameter. When the valve is closed, as shown in FIGS. 3 and 5, each leaflet folds to engage the two adjacent leaflets so that the distal edges of the leaflets are engaged from the edge of the valve to the longitudinal center $L_c$ of the valve. Thus, the engagement length shared by each distal edge of adjacent leaflets is about equal to the radius R of the valve. Since each leaflet has two engagement lengths, and there are three leaflets, the combined linear engagement length is approximately six times the valve radius, or 6R, which is the same as three times the valve diameter (3D). Since $\pi D$ is greater than 3D, the distal edge of the valve has more material than can be accommodated when the leaflets engage each other in the closed position. Thus, the excess material tended to create folds and creases during closure.

Tapering the tubular valve has been found to address and resolve this concern because extra space is provided between the valve leaflets and the aortic wall. The inflow annulus 232 of the tubular heart valve 230 is preferably sized to fit substantially flush against the aortic wall. In a straight, non-tapered tubular valve, the out-flow annulus is thus also substantially flush with the aortic wall, and there is little or no space between the leaflets, when open, and the wall. In a tapered valve, however, the out-flow annulus 234 has a diameter $D_o$ somewhat smaller than the in-flow annulus diameter $D_i$, and a space is created between the leaflets and the aortic wall at the outflow end. During valve closure, when the leaflets fold to engage each other, the seam lines of the valve can move radially outward a slight distance into the space, thereby increasing the engagement length between adjacent leaflets and accommodating the entire circumferential length ($\pi D$) of the distal outflow annulus 234 of the valve. Thus, tapering the valve minimizes folding and other disruptions that may result from limiting the space in which the distal ends of the leaflets can work.

Of course, a competing consideration when tapering the valve is interfering with the hemodynamic performance of the valve by restricting blood flow therethrough. Therefore, it is not advantageous to taper the valve any more than is needful or beneficial. Through testing and analysis, Applicants have determined that the valves are preferably tapered no more than about 10% of the in-flow diameter $D_i$; and more preferably are tapered between about 1–7%, and most preferably about 5% of the in-flow diameter $D_i$.

Figure 17:
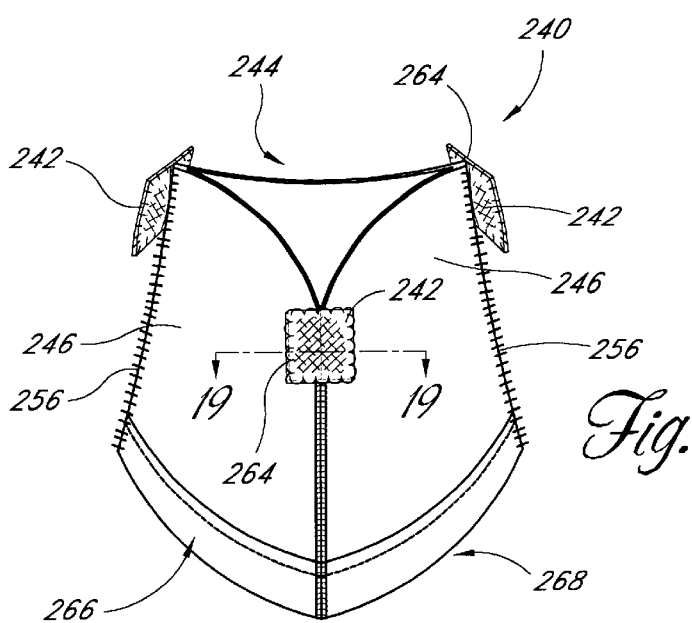
FIG. 17 shows another embodiment of a tapered aortic heart valve in a partially closed position.

FIGS. 17–19 show another embodiment of a tapered aortic valve 240. The valve has substantially rectangular commissural mounting tabs 242 at its distal end 244. FIGS. 18A–C each depict leaflets 246 that have been cut out of thin, flat, flexible material and which are used to construct the valve 240 of FIG. 17. The leaflets 246 are preferably substantially identical to one another, and each comprises a main body 250 having proximal 252 and distal ends 254 and side edges 256. The side edges 256 are slanted inwardly from the proximal end 252 towards the distal end 254 of the leaflet main body 250 so that a proximal width $W_p$ of each leaflet 246 is preferably greater than a distal width $W_d$ of each leaflet. Substantially rectangular tab portions 258 are provided adjacent the distal end 254 of each leaflet 246.

With next reference to FIG. 19, when adjacent leaflets 246 are sewn together, each tab portion 258 is folded backwards and then folded over itself so that side edges 260 of the tab portions of adjacent leaflets approximate each other. The tabs 258 are then sutured together along their side edges 260 using a plurality of stitches 262. When the tab portions 258 are stitched together as shown, they form a double-layered commissural tab 242 oriented substantially tangentially relative to the distal outflow edge 244 of the valve 240. Once the commissural tab 242 is formed, stitches 262 are placed about its outer edge 264 in order to help the tab retain its folded shape. Constructing the commissural tab 242 after this manner provides a strong, double-layered tab that, because of its substantially tangential arrangement, fits substantially flush with the aortic wall and provides a commissural attachment point that is substantially isolated from the folding valve leaflets.

FIG. 17 also shows an alternative embodiment of an in-flow annulus reinforcement structure 266. In the illustrated embodiment, the leaflet material at the in-flow annulus 268 is folded over itself a short distance and stitched in place. Preferably, the material is folded over itself a distance of about 1–5 mm and more preferably about 2–3 mm. Folding the leaflet material over itself at the in-flow annulus 268 strengthens the annulus and provides a reinforcement layer 266 to strengthen the connection between the aortic wall and the in-flow annulus 268. This fold-over reinforcement 266 can be used instead of or in addition to the cloth reinforcement 184 of FIG. 10.

With next reference to FIGS. 20–23, a mitral valve 270 may also employ an angled seam structure. Applicants have learned through testing that mitral valves tend to fold along lines that are not necessarily parallel to each other. The embodiment shown in FIG. 20 employs an angled seam arrangement 272. FIGS. 21A and 21B depict posterior and anterior valve leaflets 274, 276, respectively, of the valve 270 of FIG. 20. The width $W_{pi}$ of the in-flow edge 280 of the posterior leaflet 274 is about twice the width $W_{ai}$ of the in-flow edge 282 of the anterior leaflet 276. However, as shown in the drawings, the width $W_o$ of the out-flow edges 284, 286 of both leaflets 274, 276 is substantially the same.

With next reference to FIGS. 22 and 23, the side edges 290 of the respective leaflets 274, 276 are first aligned and then sewn with successive locked stitches 292 starting at the in-flow edges 280, 282 and progressing toward the outflow edges 284, 286 and about a tab portion 294 as discussed above. It is to be understood, however, that other embodiments can employ non-consecutive stitching, or can employ successive stitching from the out-flow edge to the in-flow edge.

Figure 24:
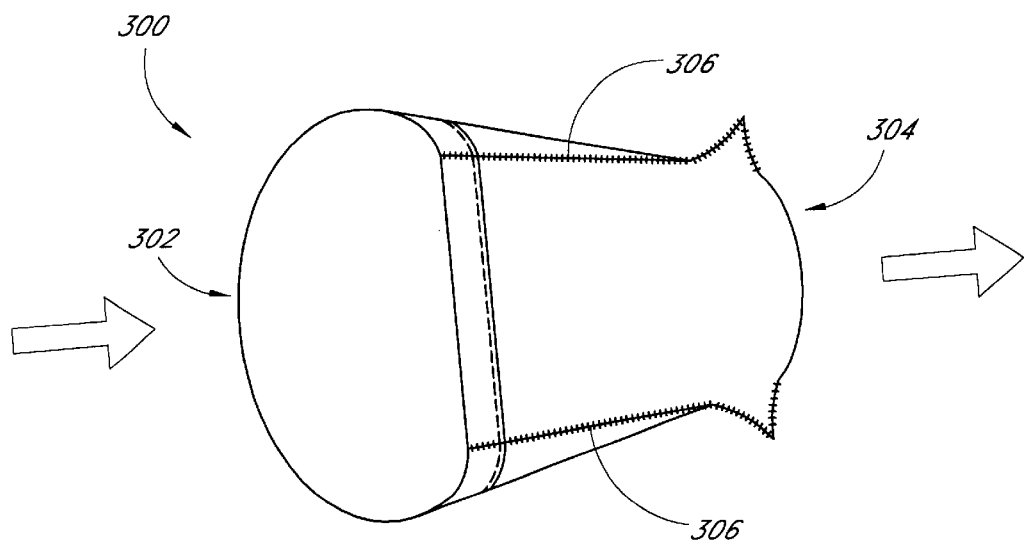
FIG. 24 shows a perspective view of a tapered prosthetic mitral heart valve having features in accordance with the present invention.
Figures 25A, 25B:
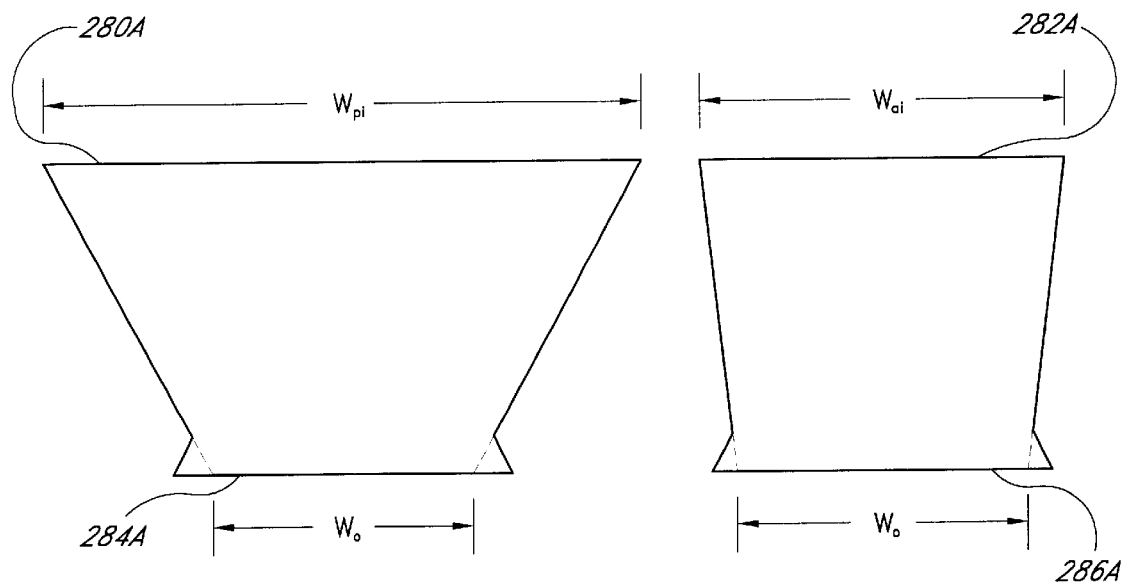
FIG. 25A shows a flat pattern for a posterior leaflet of the mitral valve of FIG. 24.
FIG. 25B shows a flat pattern of an anterior leaflet of the mitral valve of FIG. 24.

With reference next to FIGS. 24–25, another embodiment of a prosthetic mitral valve 300 having features in accordance with the present invention is provided. The mitral valve 300 is tapered from its in-flow edge 302 to its out-flow edge 304 in order to take advantage of aspects of tapered valves as discussed above with reference to FIGS. 16–19.

With specific reference to FIGS. 21A and B and 25A and B, in both of the above-described mitral valve embodiments, the width $W_o$ of the outflow edge 284, 284A of the posterior leaflet 274, 274A is substantially the same as the width $W_o$ of the outflow edge 286, 286A of the anterior leaflet 276, 276A. This is to take advantage of Applicants' discovery and observation that better closure of two-leaflet valves is observed when the widths $W_o$ of the outflow edges of the valve leaflets are substantially equal. However, in both embodiments, the seam lines 272, 306 vary in order to allow the valves 270, 300 to fold in a desired manner.

Figure 26:
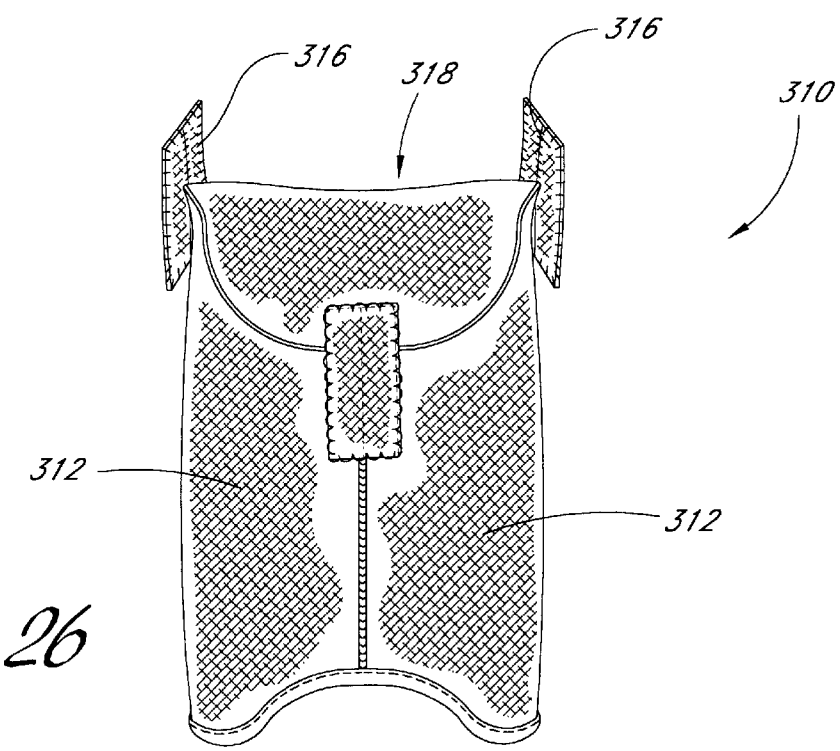
FIG. 26 shows a perspective view of yet another embodiment of an aortic heart valve having commissural tabs that extend beyond an outlet end of the valve.
Figure 27:
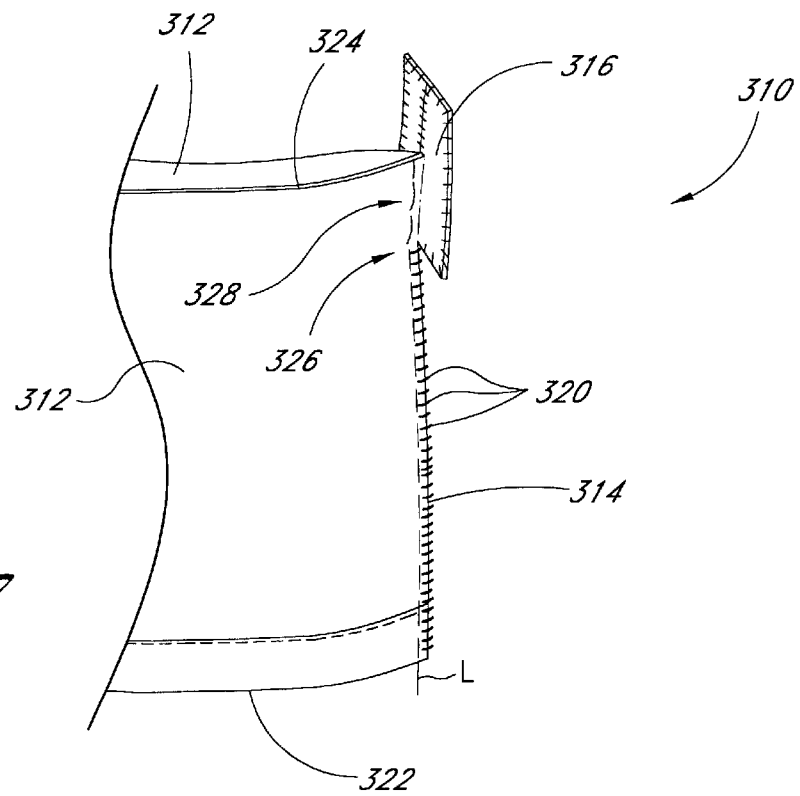
FIG. 27 shows the valve of FIG. 26 from a side view so that the manner of suturing the adjacent leaflets in the area of the commissural tabs can be seen.

With next reference to FIGS. 26 and 27, another embodiment of an aortic prosthetic heart valve 310 is provided. The valve comprises three scalloped leaflets 312 sewn together along their side edges 314 and having rectangular commissural attachment tabs 316 that are substantially tangential to the valve's outflow end 318. Adjacent leaflets 312 are attached to each other by a series of locked stitches 320 that extend from the in-flow edges 322 of the leaflets 312 toward the out-flow edges 324, terminating at a proximal end 326 of the tabs 316. The commissural tabs 316 are constructed in a folded-over manner similar to the tabs 242 of FIGS. 17–19; however, the commissural tabs 316 extend beyond the distal ends 324 of the corresponding leaflets 312. The folded-over commissural tabs 316 are preferably sewn together so as to provide a reinforcement allowing more secure commissural attachment.

As shown in FIG. 27, the locked stitches 320 do not extend along seam line L in the space 328 between the proximal end 326 of the tabs 316 and the distal end 324 of the leaflet main body. Instead, the leaflets 312 are loosely stitched together along this portion 328.

In another embodiment, no stitching is provided along the seam line L in the space 328 between the outflow end of the valve and the proximal edge of each commissural tab. Terminating locked stitches 320 and providing only minimal stitching or no stitching at all along the seam line L in the space 328 between the proximal edge 326 of the commissural tabs 316 and the outflow end 318 of the valve 310 minimizes the number of holes poked through the leaflet material. Each of these holes weakens the leaflet material. Preserving the continuity of the leaflet material in the distal portion increases the durability of the distal portion of the valve.

Forming the commissural attachment tab 316 so that it extends beyond the distal end of the leaflets 324 better distributes stresses from valve operations. As discussed above, a significant portion of the pressure that closes the valve 310 creates forces concentrated at the out-flow end 318 of the valve 310. Commissural sutures at the distal end of the valve carry this closure force. In non-raised commissural tabs, or in valve designs without tabs, the distal-most suture carries the greatest proportion of force. This arrangement can decrease durability of the leaflet about the distal-most suture. Raised tabs 316 enable the use of a plurality of stitches to secure the commissural tab 316 to the aortic wall. The closure forces that are concentrated at the out-flow ends 324 of the valve leaflets 312 will be distributed over this plurality of stitches, which are placed on the raised portion of the tab 316 distal of the out-flow end 324. Additionally, the commissural sutures are spaced from the folding leaflets 312 and do not interfere with leaflet operation.

It is to be understood that various types and shapes of commissural attachment tabs may be used in both semilunar and atrioventricular artificial valves. In semilunar valves, such as the aortic valve, the commissural tabs attach the valve to the aortic walls. In atrioventricular valves, such as the mitral valve, the commissural tabs connect the valve to chordae tendineae and/or papillary muscles. The commissural tabs for such atrioventricular valves can be shaped in any preferred way to accommodate this type of connection.

Figure 28:
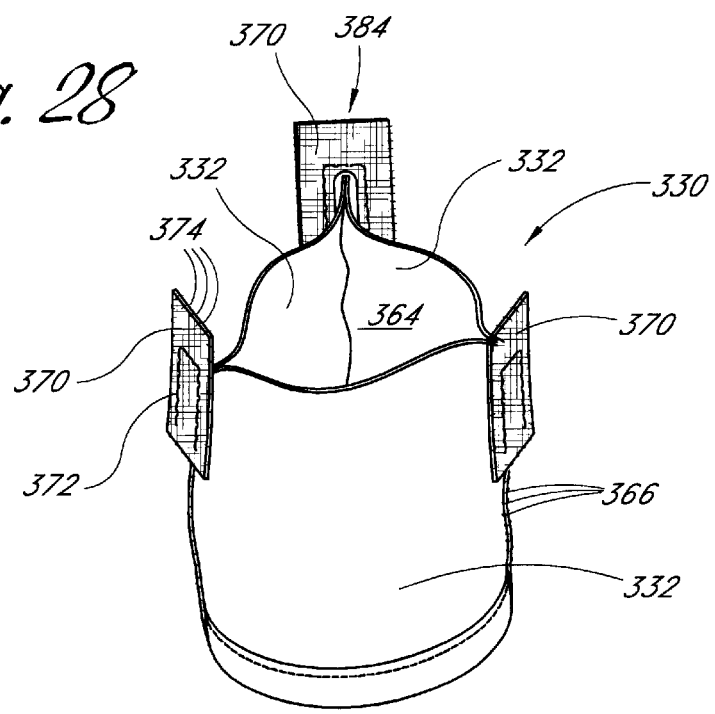
FIG. 28 shows a perspective view of still another embodiment of a tubular prosthetic aortic heart valve having features in accordance with the present invention and having commissural tabs adapted to maximize durability and hemodynamic efficiency.
Figure 29:
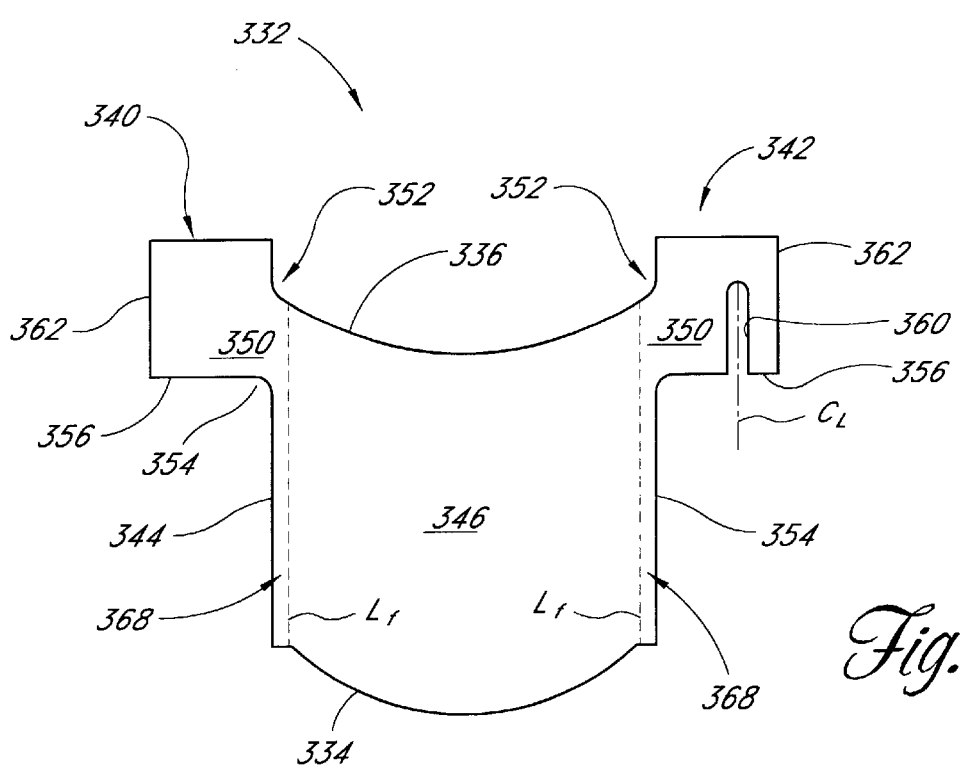
FIG. 29 shows a flat pattern for a leaflet to be used in constructing the tubular prosthetic aortic heart valve of FIG. 28.

With next reference to FIGS. 28–41, another embodiment of an aortic tubular heart valve 330 is presented. With first reference to FIGS. 28 and 29, the aortic heart valve 330 comprises three leaflets 332 that are cut out of a generally flat, flexible material along the leaflet pattern of FIG. 29. As shown, each leaflet 332 is scalloped at both its proximal and distal ends 334, 336. Distal tab portions 340, 342 extend outwardly from side edges 344 of each leaflet's main body 346. Both tabs 340, 342 are substantially rectangular in shape and extend distally beyond the distal end 336 of the main body 346. An inner edge 348 of each tab 340, 342 is preferably aligned with or aligned barely outwardly from the outer side edge 344 of the main body 346.

Each of the tabs 340, 342 communicate with the leaflet main body 346 through a neck portion 350. Transition edges 352, 354 connect the inner edges 348 of each tab with the distal end 336 of the leaflet 332, and a proximal edge 356 of each tab 340, 342 with the side edge 344 of the leaflet. The transition edges 352, 354 are preferably curved in order to avoid creating a stress concentration at the point of transition.

An elongate slot 360 is formed in the second tab 342. The slot 360 extends distally from the proximal edge 356 of the tab 342 to a point just distal of the distal-most edge of the leaflet main body 346. The distal-most end of the slot 360 is preferably rounded in order to avoid stress concentrations. A longitudinal center line CL of the slot 360 is preferably positioned about 2/3 of the way from the inner edge 348 of the tab 342 to the outer edge 362 of the tab.

Figure 30:
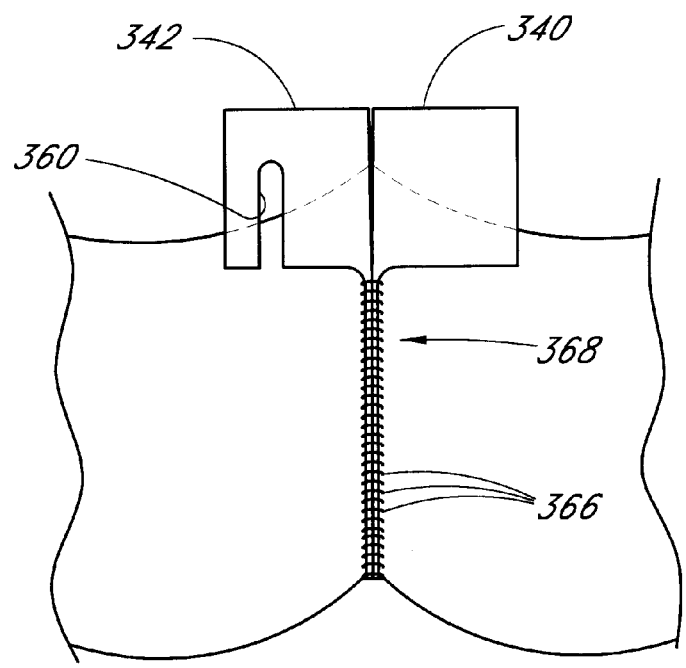
FIG. 30 shows two adjacent leaflets of the valve of FIG. 29 sutured together up to commissural tab portions.

With reference to FIG. 30, adjacent leaflets 332 are connected by bringing the outer edges 344 of the leaflets together so that the inner faces 364 of the leaflets 332 engage each other. The side edges 344 are sutured together using a series of locked stitches 366 placed between the proximal end 334 toward the distal end 336 of the leaflets 332 along a fold line $L_f$ adjacent each side edge 344. Side fold portions 368 are defined adjacent the side edges 344. It is anticipated that the fold portions 368 will fold back generally along the fold line $L_f$ when the leaflets 332 are sewn together along the side edges 344. In the illustrated embodiment, the proximal end 334 of each leaflet 332 is not scalloped in the side fold portion 368 so as to better accommodate the sutures 366 in that area.

Figure 31:
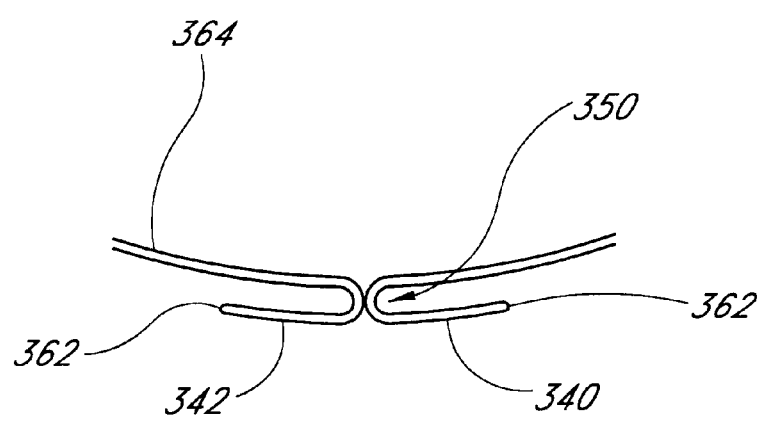
FIG. 31 is a top view showing the leaflets of FIG. 30.

The suturing terminates prior to reaching the proximal edge 356 of the tabs 340, 342, with the last suture being placed proximal of the proximal transition edge 354. The tabs 340, 342 are then folded backwardly along the fold line $L_f$ so as to overlap the outer surface 369 of their respective leaflets 332, as shown in FIGS. 30 and 31. As shown, the adjacent first and second tabs 340, 342 are folded in their neck portions 360. The tab portions 340, 342 are further folded and attached to each other to form a commissural attachment tab 370 which is adapted to avoid stress concentrations and to maximize valve durability. The manner of construction of the commissural tabs 370 is discussed below.

Figure 32:
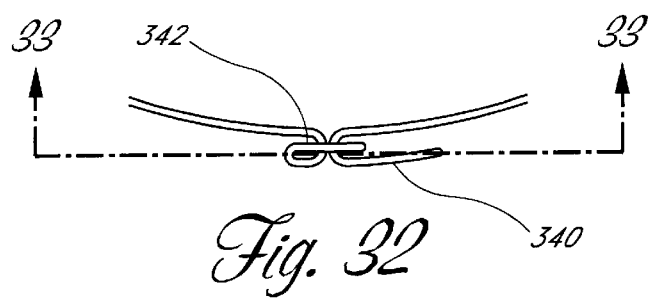
FIG. 32 is a top view showing the leaflets of FIG. 30, with a second tab of one of the leaflets folded backward.
Figure 33:
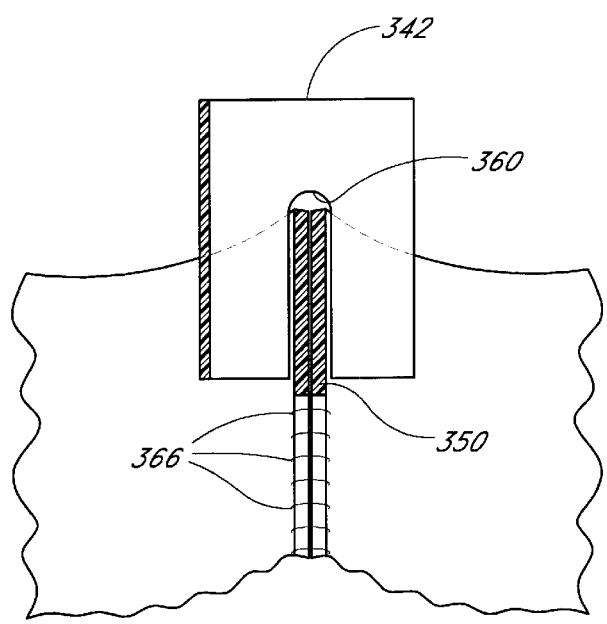
FIG. 33 is a view of the leaflets of FIG. 32, taken along line 33—33.
Figure 34:
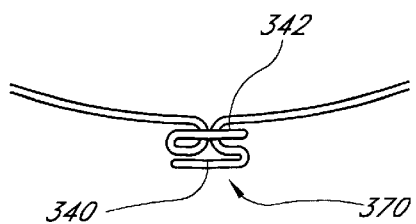
FIG. 34 is a top view showing the leaflets of FIG. 30, folded over each other in a desired manner to form a commissural tab.

With next reference to FIGS. 32 and 33, the second tab 342 is bent backwardly so that the slot 360 fits over the folded neck portions 350 of both tabs. FIG. 34 shows that the first tab 340 is then folded over to roughly approximate the second tab 342. Once the tabs have been folded over each other, minor adjustments in tab folding can be made until the overall commissural tab 370 is roughly centered along the line where the neck portions 350 of the adjacent tabs 332 fold adjacent each other. The slot 360 is preferably sized so that the second tab 342 substantially surrounds, but does not contact, the leaflet neck portions 350 so that the second tab 342 does not interfere with leaflet operation.

Figure 35:
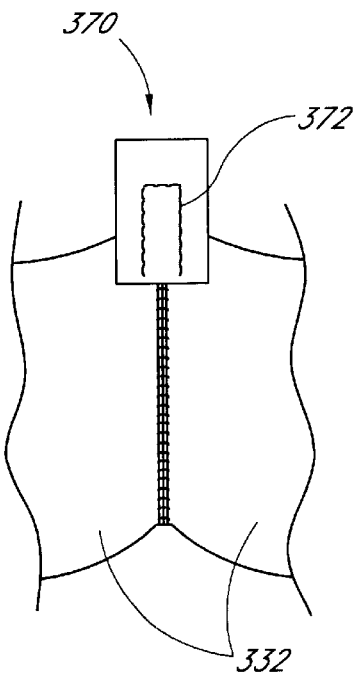
FIG. 35 shows the commissural tab of FIG. 34 sutured together.
Figure 36:
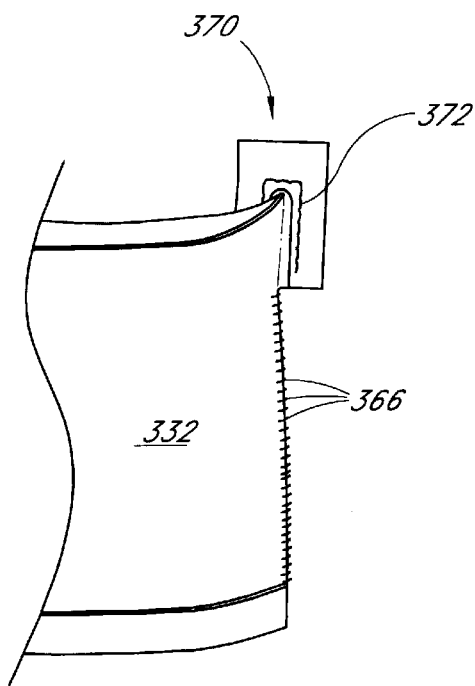
FIG. 36 shows another view of the leaflets and commissural tab of FIG. 35.
Figure 37:
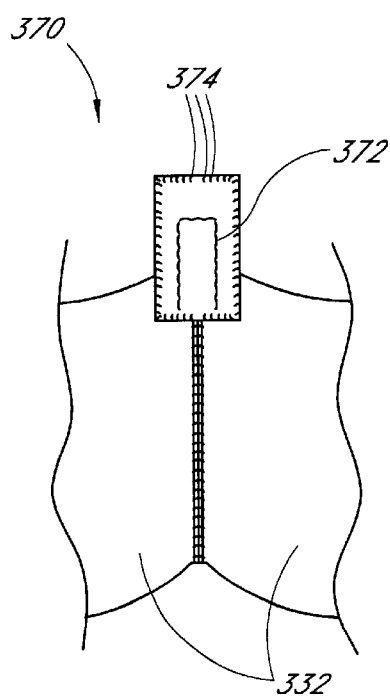
FIG. 37 shows yet another view of the commissural tab of FIG. 35 having suturing about the outer edges.

With next reference to FIGS. 35–37, once the tabs 340, 342 are properly aligned and folded over each other to create a suitable commissural attachment tab 370, an inverted U-shaped stitch line 372 is sewn through the tabs 340, 342 to connect the tabs to each other. As shown in FIG. 36, the suturing is preferably substantially parallel to, but spaced from, the slot 360 so that the first and second tabs 340, 342 are securely sutured together, but no stitching is placed in the neck portions 350 of the tabs.

To further hold the tabs together and to provide a clean, compact edge arrangement, edge suturing 374 is provided about the perimeter of each commissural attachment tab 370, as shown in FIG. 37.

As discussed above, the distal-most portion of the valve bears a significant proportion of the closure forces exerted when differential pressures cause the valve to close during operation. Since adjacent leaflets 332 are not sewn together in the neck portion 350, which is the distal-most portion of the valve leaflets 332, the leaflet material in the neck is contiguous, and there are no stress concentration points (such as punctures made to accommodate sutures) that would decrease valve durability. Also, there are no sutures along the fold line Lf in the distal portion 350 to interfere with the opening and closure of the valve 330 during operation. Further, the folded-over construction of the commissural attachment tab 370 enables the tab to accommodate numerous sutures to distribute the closure forces without interfering with operation of the valve.

Figure 38:
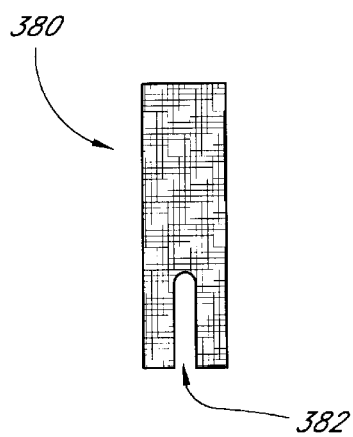
FIG. 38 shows a reinforcement member adapted to be used in connection with the commissural tab of FIG. 35.
Figure 39:
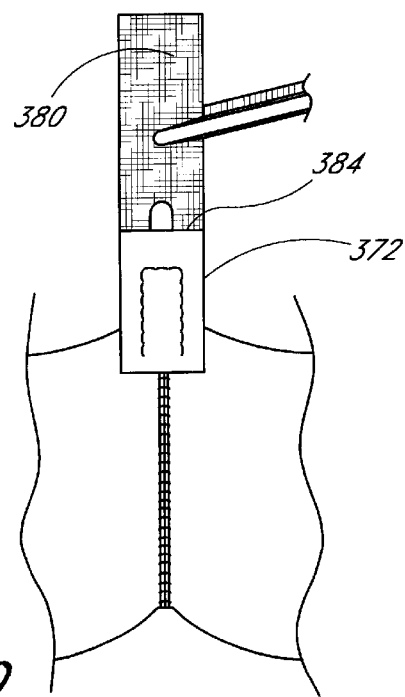
FIG. 39 shows the reinforcement member of FIG. 38 being installed on the commissural tab of FIG. 35.
Figure 40:
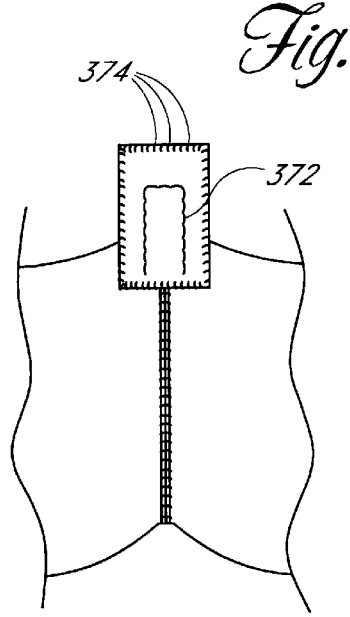
FIG. 40 shows the reinforcement member of FIG. 38 as installed on the commissural tab of FIG. 35.

Yet another embodiment provides further reinforcement for the commissural tab 370. With reference next to FIGS. 38 and 39, a woven cloth reinforcement member 380 has a slot portion 382. The slot portion 382 is sized and arranged to fit over the neck portions 350 of the leaflets 332 and the reinforcement member 380 can be folded over the distal edge 384 of the commissural tab 370. After being folded over the commissural tab 370, the reinforcement member 380 is sutured onto the tab 370, as shown in FIG. 40, in which the edge suturing 374 is placed on the tab 370 after the reinforcement member 380 is folded into place.

Figure 41:
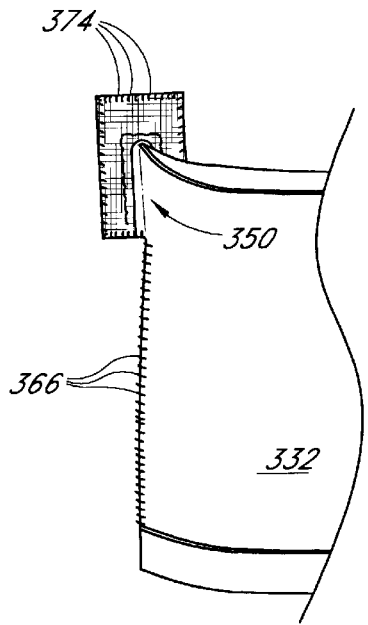
FIG. 41 shows another view of adjacent leaflets of the valve of FIG. 28, showing a reinforcement member installed on a commissural tab.

With next reference to FIG. 41, the reinforcement slot 382 is preferably sized to provide a space between the cloth 380 and the neck portions 350 of the leaflets 332 so that the reinforcement member 380 substantially does not touch the neck portions 350 when the leaflets 332 open and close. This reduces friction and further avoids stress concentrations.

After the commissural tabs 370 are sewn into place on the aortic wall, fibrous tissue will grow into and around the woven cloth of the reinforcement layer, further securing the commissural tabs in place. Additionally, endothelial cells can insulate blood flow from contact with the woven cloth material. Thrombogenesis is thus minimized and durability is maximized.

The illustrated commissural tabs have a generally rectangular construction. It is to be understood, however, that various shapes and sizes of folded commissural attachment tabs may be provided in order to accommodate other valve arrangements and types, such as atrioventricular valves, wherein the commissural tabs attach to chordae tendineae and papillary muscles.

To maximize consistency and quality when constructing valves, the shape of each leaflet is preferably substantially identical. Various cutting media and methods, such as a razor, die-cutter, laser, or jet of fluid and/or particles, can be used to obtain repeatable, precise cutting of leaflets.

Equine pericardium has a laminar structure with three layers: the visceral, serosa, and parietal layers. Applicants have discovered that cutting the equine pericardium using a contact-type cutter such as a razor or a cutting die has a tendency to delaminate one or more of the layers along the cut edges. This is because the contact-type cutting mechanism exerts relatively high forces on the leaflet material. Delaminations can disrupt valve operation and significantly impair valve durability. For example, blood can enter between delaminated layers, causing a cuspal hematoma or leading to calcification of the valve due to increased turbulence. Accordingly, it is desirable to reduce or eliminate delamination of the pericardium layers when constructing valves.

In a preferred embodiment, a non-contact cutter, such as a carbon dioxide laser having a pulse duration shorter than the thermal relaxation point of equine pericardium is used to cut individual leaflets out of flat sheets of equine pericardium. The pulse duration and power of the laser are chosen so that layers of the pericardium are substantially fused together along the cut edges, but are not burned excessively so as to damage or deform the leaflets or to create excessive carbonization. Since the laminar layers are fused together along their edges, the problem of delamination is resolved by using the laser in this arrangement.

A pulsed laser also works well for cutting the woven cloth of the reinforcement member. Such laser cutting can create a hem or bead on the cloth so that the ends of the cloth do not fray. Durability is increased and thrombogenicity is minimized by eliminating fraying.

Varying certain laser parameters, such as pulse power, cutting speed, and pulses per inch enables an operator to choose a number of arrangements that will provide appropriate cutting and fusing of pericardium layers, as well as cloth reinforcement members.

In a preferred embodiment, a plotted laser cutter, such as an M-series laser available from Universal Laser Systems of Scottsdale, Ariz., is used to precisely cut leaflets out of flat layers of equine pericardium. The plotter is preferably controlled by a computer in order to provide precision and repeatability.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof in addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A stentless prosthetic heart valve, comprising:
a plurality of thin, flexible leaflets, each of the leaflets having an inner face, an outer face, an in-flow edge, an out-flow edge, and side edges, the plurality of leaflets being sewn directly together along at least a portion of their side edges so as to form a substantially tubular valve structure having an in-flow end and an out-flow end, adjacent leaflets being arranged so that their side edges are substantially aligned and the inner faces of the leaflets engage each other adjacent the side edges,
wherein the valve structure is movable between a closed position in which the out-flow edges of adjacent leaflets engage each other, and an open position in which the out-flow edges of adjacent leaflets are separated from each other except along the side edges, the sewn portions of the side edges of the leaflets biasing the leaflets toward a partially closed position.

2. A heart valve as in claim 1, wherein the aligned leaflet side edges extend generally outwardly from the substantially tubular valve structure.

3. A heart valve as in claim 1, wherein each of the leaflets comprises a tab portion adjacent the leaflet out-flow edge.

4. A heart valve as in claim 3, wherein each tab portion extends beyond the out-flow edge of a corresponding leaflet.

5. A heart valve as in claim 3, wherein the tab portions are disposed adjacent at least one of the leaflet side edges.

6. A heart valve as in claim 5, wherein a tab portion is formed adjacent each leaflet side edge.

7. A heart valve as in claim 6, wherein the tab portions of adjacent leaflets are connected to each other to form commissural attachment tabs.

8. A heart valve as in claim 7, wherein the connected tab portions are at least partially folded over each other.

9. A heart valve as in claim 7 additionally comprising reinforcement material over the commissural attachment tabs.

10. A heart valve as in claim 7, wherein the commissural tabs extend distally beyond the out-flow end of the tubular valve structure.

11. A heart valve as in claim 6, wherein each commissural tab substantially lies in a plane generally tangential to the tubular valve structure when the valve structure is in the open position.

12. A heart valve as in claim 1, wherein each of the leaflets are substantially identical.

13. A heart valve as in claim 1 comprising a first leaflet and a second leaflet, and a width of the in-flow edge of the first leaflet is greater than a width of the in-flow edge of the second leaflet.

14. A heart valve as in claim 13, wherein a width of the out-flow edge of the first leaflet is substantially the same as a width of the out-flow edge of the second leaflet.

15. A heart valve as in claim a additionally comprising a cloth reinforcement member attached to the valve in-flow end.

16. A stentless semilunar heart valve, comprising:
three thin, flexible leaflets, each of the leaflets having an inner face, an outer face, an in-flow edge, an out-flow edge, side edges, and tab portions extending outwardly beyond the side edges and positioned adjacent the out-flow edge, the leaflets being sewn directly to each other along their side edges so as to form a substantially tubular valve structure having an in-flow and an out-flow end;
wherein the tab portions of adjacent leaflets engage each other to form commissural attachment tabs, at least a portion of each commissural attachment tab being adjacent the outer faces of the adjacent leaflets.

17. A semilunar heart valve as in claim 16, wherein the three leaflets are substantially identical to each other.

18. A semilunar heart valve as in claim 16, wherein adjacent leaflets are arranged so that their side edges are substantially aligned and the leaflet inner faces engage each other adjacent the side edges, and a plurality of stitches are disposed along a line adjacent the aligned side edges.

19. A semilunar heart valve as in claim 18, wherein a portion of a line adjacent the out-flow edges of the leaflets has no stitches therein.

20. A semilunar heart valve as in claim 16, wherein the tab portions of adjacent leaflets overlap each other so that each commissural tab has multiple layers.

21. A semilunar heart valve as in claim 20 additionally comprising a cloth reinforcement member attached to the commissural attachment tabs.

22. A semilunar heart valve as in claim 16, wherein a diameter of the inflow end of the valve structure is greater than a diameter of the out-flow end of the valve structure.

23. A semilunar heart valve as in claim 16, wherein the in-flow edge and out-flow edge of each leaflet has a substantially scalloped shaped.

24. A semilunar heart valve as in claim 23, wherein a center portion of the in-flow edge of each leaflet extends a distance proximal of a position at which the side edge meets the in-flow edge.

25. A semilunar heart valve as in claim 24, wherein a center portion of the out-flow edge of each leaflet extends a proximal of a position which the side edge meets the out-flow edge.

26. A stentless heart valve, comprising:
a first leaflet comprising a leaflet main body having an inner face, an outer face, a proximal end, a distal end, a first side edge, and a first tab portion adjacent the distal end and extending outwardly from the first side edge, the first tab portion connected to the first leaflet main body through a first neck portion; and
a second leaflet comprising a leaflet main body having an inner face, an outer face, a proximal end, a distal end, a second side edge, and a second tab portion adjacent the distal end extending from the second side edge, the second tab portion having a longitudinal slot and connected to the second leaflet main body through a second neck portion;
the first side edge of the first leaflet and the second side edge of the second leaflet being substantially aligned with and attached to one another and the inner faces of the first leaflet and the second leaflet engaging each other adjacent the aligned side edges; and
wherein the second tab portion is folded so that the first and second neck portions extend through the longitudinal slot of the second tab portion.

27. A heart valve as in claim 26, wherein the first tab portion is folded over the second tab portion.

28. A heart valve as in claim 26, wherein the first and second neck portions are not stitched.

29. A heart valve as in claim 26, wherein the first and second tab portions are sewn together to form a commissural attachment tab.

30. A heart valve as in claim 29, wherein the commissural attachment tab is adapted to be attached to an inner wall of a blood vessel.

31. A heart valve as in claim 26, wherein the tabs, neck and main body of each leaflet are unitarily formed.

32. A heart valve as in claim 26, wherein the proximal and distal ends of he leaflet are scalloped.

33. A method for making a stentless tubular prosthetic hear valve, comprising:
providing a section of substantially flat, flexible material;
cutting a plurality of leaflets out of the flat material, each of the leaflets having an inner face, an outer face, a proximal end, a distal end, side edges, and tab portions adjacent the distal end and tending from the side edges;
aligning the side edges of adjacent leaflets together so that the inner faces of adjacent leaflets engage each other adjacent the side edges; and
sewing aligned side edges together so as to form a substantially tubular valve structure having an in-flow and an out-flow end.

34. The method of claim 33, wherein providing a section of substantially flat, flexible material involves providing a section of pericardium and fixing the pericardium.

35. The method of claim 34, wherein the material is equine pericardium.

36. The method of claim 33, wherein cutting a plurality of leaflets is accomplished using a non-contact cutting apparatus.

37. The method of claim 36, wherein cutting a plurality of leaflets is accomplished using a laser.

38. The method of claim 33 additionally comprising folding the tab portions of the leaflets to form a commissural tab.

39. A method of manufacturing a stentless prosthetic heart valve comprising:
providing a first valve leaflet and a second valve leaflet, the leaflets being formed separately from each other;
placing a portion of an inward face of the first valve leaflet against a corresponding portion of an inward face of the second valve leaflet; and
attaching the inward face portions to each other wherein the inward face portions of the leaflets are attached at the side edges of the leaflets.

40. The method of claim 39 additionally comprising forming the valve leaflets from equine pericardium.

41. The method of manufacturing a stentless prosthetic valve comprising providing first and second valve leaflets each having an integral tab portion at an end thereof; and
folding the tab portions relative to each other to provide a commissural tab, the commissural tab being attached to the leaflets along a commissural tab line such that free ends of the tabs extend substantially radially outwardly from the line; and
additionally comprising attaching side edges of the valve leaflets to each other along an attachment line which is coextensive with the commissural tab line.

42. A stentless prosthetic comprising:
a plurality of valve leaflets comprised of a flexible material, each leaflet having an inner surface and an outer surface, each leaflet sewn directly to another leaflet along an attachment line, a portion of an inner surface face of one leaflet being in facing relationship with a portion of an inner surface of another leaflet at the attachment line; and
a commissural tab at an end of each attachment line, said tab configured for attachment to tissue.

43. The valve of claim 42, wherein the commissural tab is comprised of a flexible material.

44. The valve of claim 42, wherein the commissural tab is integral with the valve leaflet.

45. The valve of claim 42, wherein the leaflets are comprised of pericardial tissue.

46. The valve of claim 45, wherein the leaflets are comprised of equine pericardium.

47. A prosthetic valve comprising: a valve body comprising at least first and second leaflets joined along a leaflet attachment line, said valve body comprising an inlet and an outlet, said leaflet attachment line extending from the inlet towards said outlet and terminating at a location short of the outlet, said valve body including a commissural tab comprised of neck portions juxtaposed along a neck line that extends from the attachment line termination to said outlet, said neck portions being at least substantially unattached along said neck line.

48. The valve of claim 47, comprising a third leaflet joined to the first and second leaflets.

49. The valve of claim 47, wherein said leaflets are scalloped.

50. The valve of claim 49, wherein the scallops are on the outflow end of the valve.

51. The valve of claim 49, wherein the scallops are on the inflow end of the valve.

52. The valve of claim 49, wherein the scallops are on both ends of the valve.

53. The valve of claim 47, wherein the leaflets are joined along the attachment line by stitches.

54. The valve of claim 47, wherein said neck portions are disposed in a slot in said commissural tab, said slot retaining said neck portions in said juxtaposed relationship without attachment to each other.

55. The valve of claim 54, wherein a distal end of the slot is rounded to avoid stress concentrations.

56. The valve of claim 54, wherein said tab is stitched on opposite sides of said slot along respective lines that are spaced relative to said slot such that no stitches are in said neck portions.

57. A prosthetic valve, comprising:
a valve body having an inlet portion comprising an annulus and an outlet portion, said annulus having a periphery comprised of edges which are scalloped.

58. The valve of claim 57, wherein the outlet portion includes at least two commissural attachment locations.

59. The valve of claim 57, wherein the edges of the outlet portion bare scalloped.

60. The valve of claim 57, wherein said valve body comprises at least two leaflets joined to each other by seams extending longitudinally along the valve body.

61. The valve of claim 60, wherein the seams retain an interior side of one leaflet in facing relationship with an interior side of another leaflet.

62. A stentless prosthetic heart valve, comprising:
a plurality of thin, flexible leaflets, each of the leaflets having an inner face, an outer face, an in-flow edge, an out-flow edge, and side edges, the plurality of leaflets being sewn together along at least a portion of their side edges so as to form a substantially tubular valve structure having an in-flow end and an out-flow end, adjacent leaflets being arranged so that their side edges are substantially aligned and the inner faces of the leaflets engage each other adjacent the side edges,
wherein the valve structure is movable between a closed position in which the out-flow edges of adjacent leaflets engage each other, and an open position in which the out-flow edges of adjacent leaflets are separated from each other except along the side edges, the sewn portions of the side edges of the leaflets biasing the leaflets toward a partially closed position,
wherein the leaflets comprises a tab portion adjacent the leaflet out-flow edge, the tab portions are disposed adjacent at least one of the leaflet side edges, the tab portion is formed adjacent each leaflet side edge, the tab portions of adjacent leaflets are connected to each other to form commissural attachment tabs;
wherein the connected tab portions are at least partially folded over each other.

63. A stentless semilunar heart valve, comprising:
three thin, flexible leaflets, each of the leaflets having an inner face, an outer face, an in-flow edge, an out-flow edge, side edges, and tab portions extending outwardly beyond the side edges and positioned adjacent the out-flow edge, the leaflets being attached to each other along their side edges so as to form a substantially tubular valve structure having an in-flow and an out-flow end;
wherein the tab portions of adjacent leaflets engage each other to form commissural attachment tabs, at least a portion of each commissural attachment tab being adjacent the outer faces of the adjacent leaflets;
wherein the in-flow edge and out-flow edge of each leaflet has a substantially scalloped shaped, a center portion of the in-flow edge of each leaflet extends a distance proximal of a position at which the side edge meets the in-flow edge;
wherein a center portion of the out-flow edge of each leaflet extends a proximal of a position which the side edge meets the out-flow edge.

64. A prosthetic valve comprising:
a valve body comprising at least first and second leaflets joined along a leaflet attachment line, said valve body comprising an inlet and an outlet, said leaflet attachment line extending from the inlet towards said outlet and terminating at a location short of the outlet, said valve body including a commissural tab comprised of neck portions juxtaposed along a neck line that extends from the attachment line termination to said outlet, said neck portions being at least substantially unattached along said neck line;
wherein the leaflets are joined along the attachment line by stitches.

65. A prosthetic valve comprising:
a valve body comprising at least first and second leaflets joined along a leaflet attachment line, said valve body comprising an inlet and an outlet, said leaflet attachment line extending from the inlet towards said outlet and terminating at a location short of the outlet, said valve body including a commissural tab comprised of neck portions juxtaposed along a neck line that extends from the attachment line termination to said outlet, said neck portions being at least substantially unattached along said neck line;
wherein said neck portions are disposed in a slot in said commissural tab, said slot retaining said neck portions in said juxtaposed relationship without attachment to each other;
wherein a distal end of the slot is rounded to avoid stress concentrations.

66. A prosthetic valve comprising:
a valve body comprising at least first and second leaflets joined along a leaflet attachment line, said valve body comprising an inlet and an outlet, said leaflet attachment line extending from the inlet towards said outlet and terminating at a location short of the outlet, said valve body including a commissural tab comprised of neck portions juxtaposed along a neck line that extends from the attachment line termination to said outlet, said neck portions being at least substantially unattached along said neck line;
wherein said neck portions are disposed in a slot in said commissural tab, said slot retaining said neck portions in said juxtaposed relationship without attachment to each other;
wherein said tab is stitched on opposite sides of said slot along respective lines that are spaced relative to said slot such that no stitches are in said neck portions.

* * * * *